US010919867B2

(12) United States Patent
Volp et al.

(10) Patent No.: US 10,919,867 B2
(45) Date of Patent: Feb. 16, 2021

(54) SUBSTITUTED BENZOTRIAZOLE PHENOLS

(71) Applicant: 3M INNOVATIVE PROPERTIES COMPANY, St. Paul, MN (US)

(72) Inventors: Kelly A. Volp, Minneapolis, MN (US); Nathan E. Schultz, Woodbury, MN (US); Fuming B. Li, Woodbury, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 15/741,647

(22) PCT Filed: Jun. 30, 2016

(86) PCT No.: PCT/US2016/040348
§ 371 (c)(1),
(2) Date: Jan. 3, 2018

(87) PCT Pub. No.: WO2017/007672
PCT Pub. Date: Jan. 12, 2017

(65) Prior Publication Data
US 2018/0186757 A1 Jul. 5, 2018

Related U.S. Application Data

(60) Provisional application No. 62/189,533, filed on Jul. 7, 2015.

(51) Int. Cl.
C07D 249/20 (2006.01)
C07D 403/12 (2006.01)
C07B 41/04 (2006.01)
C07B 43/04 (2006.01)
C07B 45/04 (2006.01)
C07B 45/06 (2006.01)
C07B 51/00 (2006.01)

(52) U.S. Cl.
CPC ............ *C07D 249/20* (2013.01); *C07B 41/04* (2013.01); *C07B 43/04* (2013.01); *C07B 45/04* (2013.01); *C07B 45/06* (2013.01); *C07B 51/00* (2013.01); *C07D 403/12* (2013.01)

(58) Field of Classification Search
None
See application file for complete search history.

(56) References Cited

U.S. PATENT DOCUMENTS

| 30,782 A | 11/1860 | Wright |
|---|---|---|
| 31,285 A | 1/1861 | Miller |
| 32,171 A | 4/1861 | Alexander |
| 3,004,896 A | 10/1961 | Heller |
| 3,971,373 A | 7/1976 | Braun |
| 4,100,324 A | 7/1978 | Anderson |
| 4,118,531 A | 10/1978 | Hauser |
| 4,215,682 A | 8/1980 | Kubik |
| 4,251,435 A | 2/1981 | Son |
| 4,264,750 A | 4/1981 | Anand |
| 4,340,563 A | 7/1982 | Appel |
| 4,375,718 A | 3/1983 | Wadsworth |
| 4,429,001 A | 1/1984 | Kolpin |
| 4,508,781 A | 4/1985 | Yagi |
| 4,557,945 A | 12/1985 | Yagi |
| 4,588,537 A | 5/1986 | Klaase |
| 4,592,815 A | 6/1986 | Nakao |
| 4,652,282 A | 3/1987 | Ohmori |
| 4,789,504 A | 12/1988 | Ohmori |
| 4,874,659 A | 10/1989 | Ando |
| 5,030,731 A | 7/1991 | Slongo |
| 5,057,710 A | 10/1991 | Nishiura |
| 5,096,977 A | 3/1992 | MacLeay |
| 5,124,723 A | 6/1992 | Laver |
| 5,233,047 A | 8/1993 | MacLeay |
| 5,401,446 A | 3/1995 | Tsai |
| 5,496,507 A | 3/1996 | Angadjivand |
| 5,663,128 A | 9/1997 | Evans et al. |
| 5,871,845 A | 2/1999 | Dahringer |
| 5,908,598 A | 6/1999 | Rousseau |
| 5,914,186 A | 6/1999 | Yau |
| 5,919,847 A | 7/1999 | Rousseau |
| 5,922,882 A | 7/1999 | Mori |
| 5,968,635 A | 10/1999 | Rousseau |
| 5,976,208 A | 11/1999 | Rousseau |
| 6,213,122 B1 | 4/2001 | Rousseau |
| 6,214,094 B1 | 4/2001 | Rousseau |
| 6,238,466 B1 | 5/2001 | Rousseau |
| 6,268,495 B1 | 7/2001 | Rousseau |
| 6,361,764 B2* | 3/2002 | Richard .............. A61K 8/4966 424/400 |

(Continued)

FOREIGN PATENT DOCUMENTS

| EP | 0351732 | 1/1990 |
|---|---|---|
| EP | 0447166 | 9/1991 |

(Continued)

OTHER PUBLICATIONS

Database Registry Chemical Abstracts Service, Columbus, Ohio, Accession No. RN 53012-54-7, Entered STN: Nov. 16, 1984.*
Grant & Hackh's Chemical Dictionary (5th Ed. 1987) at p. 148.*
Database Registry Chemical Abstracts Service, Columbus, Ohio, Accession No. RN 185460-78-0, Entered STN: Jan. 29, 1997.*
Database Registry Chemical Abstracts Service, Columbus, Ohio, Accession No. RN 95733-13-4, Entered STN: Apr. 6, 1985.*
Antalek, "Using pulsed gradient spin echo NMR for chemical mixture analysis: How to obtain optimum results", Concepts in Magnetic Resonance, 2002, vol. 14, No. 4, pp. 225-258.
Auge, "NMR Measure of Translational Diffusion and Fractal Dimension. Application to Molecular Mass Measurement", The Journal of Physical Chemistry B, 2009, vol. 113, No. 7, pp. 1914-1918.

(Continued)

*Primary Examiner* — Samantha L Shterengarts
(74) *Attorney, Agent, or Firm* — Jeffrey M. Olofson

(57) ABSTRACT

Benzotriazole phenols with substituents either ortho to the phenol hydroxyl group and/or para to the phenol hydroxyl group can be prepared from the unsubstituted benzotriazole phenol by coupling reactions. The ortho substituent group can be a simple alkoxy or amino group, or the ortho substituent group can be a linking group, linking the benzotriazole phenol to another benzotriazole phenol group.

17 Claims, No Drawings

(56) References Cited

U.S. PATENT DOCUMENTS

| | | | |
|---|---|---|---|
| 6,365,088 B1 | 4/2002 | Knight |
| 6,375,886 B1 | 4/2002 | Angadjivand |
| 6,397,458 B1 | 6/2002 | Jones |
| 6,398,847 B1 | 6/2002 | Jones |
| 6,406,657 B1 | 6/2002 | Eitzman |
| 6,409,806 B1 | 6/2002 | Jones |
| 6,419,871 B1 | 7/2002 | Ogale |
| 6,432,175 B1 | 8/2002 | Jones |
| 6,451,887 B1 | 9/2002 | Wood |
| 6,454,986 B1 | 9/2002 | Eitzman |
| 6,524,488 B1 | 2/2003 | Insley |
| 6,562,112 B2 | 5/2003 | Jones |
| 6,607,624 B2 | 8/2003 | Berrigan |
| 6,660,210 B2 | 12/2003 | Jones |
| 6,743,464 B1 | 6/2004 | Insley |
| 6,789,241 B2 | 9/2004 | Anderson |
| 6,800,676 B2 | 10/2004 | Wood |
| 6,808,551 B2 | 10/2004 | Jones |
| 6,824,718 B2 | 11/2004 | Eitzman |
| 6,916,752 B2 | 7/2005 | Berrigan |
| 7,244,291 B2 | 7/2007 | Spartz |
| 7,244,292 B2 | 7/2007 | Kirk |
| 7,390,351 B2 | 6/2008 | Leir |
| 7,765,698 B2 | 8/2010 | Sebastian |
| 8,162,153 B2 | 4/2012 | Fox |
| 8,790,449 B2 | 7/2014 | Li |
| 2002/0035175 A1 | 3/2002 | Wood |
| 2002/0115753 A1 | 8/2002 | Ravichandran |
| 2002/0174869 A1 | 11/2002 | Gahan |
| 2003/0004235 A1 | 1/2003 | Wood |
| 2003/0134515 A1 | 7/2003 | David |
| 2003/0192231 A1 | 10/2003 | Wood |
| 2003/0213164 A1 | 11/2003 | Pastor |
| 2004/0092634 A1 | 5/2004 | Arnoldi |
| 2007/0154531 A1* | 7/2007 | Hashimoto .......... A61K 9/7053 424/448 |
| 2008/0038976 A1 | 2/2008 | Berrigan |
| 2012/0302760 A1 | 11/2012 | Preschel |

FOREIGN PATENT DOCUMENTS

| | | |
|---|---|---|
| EP | 0593936 | 4/1994 |
| EP | 0623941 | 11/1994 |
| EP | 0644195 | 3/1995 |
| FR | 1324897 | 4/1963 |
| GB | 991142 | 5/1965 |
| JP | 02292357 | 12/1990 |
| JP | 06254319 | 9/1994 |
| JP | 08284063 | 10/1996 |
| JP | 2002212439 | 7/2002 |
| WO | WO 1993-14510 | 7/1993 |
| WO | WO 2001-07144 | 2/2001 |
| WO | WO 2002-14419 | 2/2002 |
| WO | WO 2002-098968 | 12/2002 |
| WO | WO 2008-131921 | 11/2008 |
| WO | WO 2009-076064 | 6/2009 |
| WO | WO 2009-148744 | 12/2009 |
| WO | WO 2009-148747 | 12/2009 |
| WO | WO 2010-114742 | 10/2010 |
| WO | WO 2011-005711 | 1/2011 |
| WO | WO 2011-137142 | 11/2011 |
| WO | WO 2012-163936 | 12/2012 |
| WO | WO 2013/060254 | 5/2013 |
| WO | WO 2014-105107 | 7/2014 |
| WO | WO 2014-172308 | 10/2014 |
| WO | WO 2017-007673 | 1/2017 |
| WO | WO 2017-007675 | 1/2017 |
| WO | WO 2017-007677 | 1/2017 |

OTHER PUBLICATIONS

Belusa, "2-(2-Hydroxyphenyl) benzotriazoles. I. Synthesis and their ultraviolet and infrared spectra", Chemicke Zvesti, 1974, vol. 28, No. 5, pp. 673-679.

Belusa, "2-(2-Hydroxyphenyl) benzotriazoles. II. Electrophilic substitution reactions on the molecule of 2-(2-hydroxy--5-methylphenyl) benzotriazole and ultraviolet spectra of the products", Chemicke Zvesti, Jan. 1974, vol. 28 No. 5, pp. 680-685.

Belusa, "Synthesis of 2,2-bis-/4-hydroxy-3,5-di-(2-benzotriazolyl) phenyl/propane", Tetrahedron Letters, 1968, vol. 9, No. 10, pp. 1167-1170.

Berliner, "Synthesis of Alpha-Halo Ethers from Symmetric Acetals and In Situ Methoxymethylation of an Alcohol", Organic Syntheses, 2007, vol. 84, pp. 102-110.

Burgos, "Significantly Improved Method for the Pd-Catalyzed Coupling of Phenols with Aryl Halides: Understanding Ligand Effects", Angewandte Chemie International Edition, Jun. 2006, vol. 45, No. 26, pp. 4321-4326.

Carofiglio, "UV stabilizers bonded to transition metals: Synthesis and X-ray structure of 2-(2'-hydroxyphenyl)benzotriazole-oxovanadium(IV) and—dioxomolybdenum(VI) complexes", Polyhedron, Sep. 1996, vol. 15, No. 24, pp. 4435-4440.

Cheung, "Palladium-Catalyzed Hydroxylation of Aryl and Heteroaryl Halides Enabled by the Use of a Palladacycle Precatalyst", The Journal of Organic Chemistry, Apr. 2012, vol. 79, No. 11, pp. 5351-5358.

Davies, "The Separation of Airborne Dust and Particles," Proceedings of the Institution of Mechanical Engineers, Part B: Journal of Engineering Manufacture, 1952, vol. 1B, pp. 185-198.

Dennis, "Procyanidin oligomers. A new method for 4→8 interflavan bond formation using C8-boronic acids and iterative oligomer synthesis through a boron-protection strategy", Tetrahedron, Jan. 2012, vol. 68, No. 1, pp. 340-348.

Evans, "Synthesis of diaryl ethers through the copper-promoted arylation of phenols with arylboronic acids. An expedient synthesis of thyroxine", Tetrahedron Letters, 1998, vol. 39, No. 19, pp. 2937-2940.

Kürti, Strategic Applications of Named Reactions in Organic Synthesis, 2005, pp. 464-465.

Li, "Synthesis and structural characterization of zinc complexes supported by amino-benzotriazoie phenoxide ligands: Efficient catalysts for ring-opening polymerization of ϵ-caprolactone and β-butyrolactone", Inorganic Chemistry Communications, 2011, vol. 14, No. 07, pp. 1140-1144, XP028220554.

Maliakal, "Twisted Intramolecular Charge Transfer States in 2-Arylbenzotriazoles: Fluorescence Deactivation via Intramolecular Electron Transfer Rather Than Proton Transfer", Journal of Physical Chemistry A, 2002, vol. 106, No. 34, pp. 7680-7689, XP055294802.

Matteucci, Mild and Highly Chemoselective Oxidation of Thioethers Mediated by $Sc(OTf)_3$, Organic Letters, 2003, vol. 5, No. 3, pp. 235-237.

Neufeld, "Accurate molecular weight determination of small molecules via DOSY-NMR by using external calibration curves with normalized diffusion coefficients", Chemical Science, 2015, vol. 6, pp. 3354-3364.

Nilsson, "The DOSY Toolbox: A new tool for processing PFG NMR diffusion data", Journal of Magnetic Resonance, 2009, vol. 200, No. 2, pp. 296-302.

Rosevear, "Preparation of some 2-(2' H -Benzotriazol-2'-yl)phenol ultraviolet absorbers: Application of the transalkylation reaction", Australian Journal of Chemistry, 1985, vol. 38, No. 08, pp. 1163-1176, XP055294724.

Seechurn, "Palladium-Catalyzed Cross-Coupling: A Historical Contextual Perspective to the 2010 Nobel Prize", Angewandte Chemie International Edition, May 2012, vol. 51, No. 21, pp. 5062-5085.

Valiev, "NWChem: a comprehensive and scalable open-source solution for large scale molecular simulations", Computer Physics Communications, 2010, vol. 181, No. 9, pp. 1477-1489.

Varma, "The Urea-Hydrogen Peroxide Complex: Solid-State Oxidativve Protocols for Hydroxylated Adehydes and Ketones (Dakin Reaction), Nitriles, Sulfides, and Nitrogen Heterocycles", Organic Letters, 1991, vol. 1, No. 2, pp. 189-191.

Waker, "Application of Cavity Theory to the Discharge of Electrostatic Dust Filters by x-Rays", International Journal of Radiation Applications and Instrumentation. Part A. Applied Radiation and Isotopes, 1988, vol. 39, No. 7, pp. 677-684.

(56) References Cited

OTHER PUBLICATIONS

Wente, "Superfine Thermoplastic Fibers," Industrial and Engineering Chemistry, Aug. 1956, vol. 48, No. 8, pp. 1342-1346.
Wente, "Manufacture of Superfine Organic Fibers", Report No. 4364 of the Naval Research Laboratories, May 1954, pp. 1-20.
Wu, "A Single Phosphine Ligand Allows Palladium-Catalyzed Intermolecular CO Bond Formation with Secondary and Primary Alcohols", Angewandte Chemie International Edition, Sep. 2011, vol. 50, No. 42, pp. 9943-9947.
Xu, "Synthesis of diaryl-azo derivatives as potential antifungal agents", Bioorganic & Medicinal Chemistry Letter, Jul. 2010, vol. 20, No. 14, pp. 4193-4195.
International Search Report for PCT International Application No. PCT/US2016/040348, dated Aug. 22, 2016, 6 pages.

* cited by examiner

SUBSTITUTED BENZOTRIAZOLE PHENOLS

FIELD OF THE DISCLOSURE

This disclosure relates to substituted phenol compounds, protected substituted phenol compounds, and methods of preparing substituted phenol compounds and protected substituted phenol compounds.

BACKGROUND

Phenols are class of chemical compounds having a hydroxyl group directly bonded to an aromatic hydrocarbon group. A wide variety of phenolics, as compounds that contain a phenol group are called, are known. Some phenolics are produced by plants in nature and others have been synthetically designed for a variety of chemical uses.

One class of phenolics are 2-(2-hydroxyphenyl)benzotriazoles or benzotriazole phenols. Benzotriazole phenols are an important class of UV absorbers, and in some cases, can absorb in the visible range as well. These compounds are often used as additives in materials and can even be incorporated into the polymeric structures via a polymerizable substituent on the benzotriazole phenol structure. A number of bisbenzotriazolylphenol compounds are described in U.S. Pat. No. 5,922,882 (Mori, et al.).

In addition to the usefulness of the benzotriazole phenols themselves, the benzotriazole phenols can also be used as synthons to form benzotriazole phenolate salts that are also useful. For example in EP Patent Publication No. 351,732, the use of a variety of benzotriazole phenolate salts are used as the essential ingredient to give high crystallization rates in polyester polymer compositions.

The need remains for substituted benzotriazole phenols for a variety of uses and as synthons for benzotriazole phenolate salts.

SUMMARY

Disclosed herein are benzotriazole phenol compounds, protected benzotriazole phenol compounds, and methods for preparing benzotriazole phenol compounds and protected benzotriazole phenol compounds.

Among the embodiments disclosed herein are compositions comprising a substituted or unsubstituted benzotriazole phenol with the structure of Formula I:

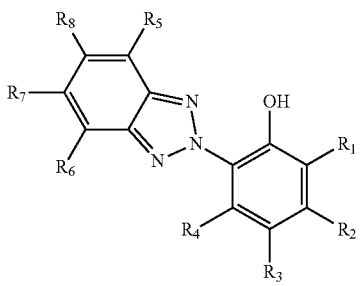

Formula I wherein if $R^1$ comprises a hydrogen atom; $R^3$ comprises an alkoxy or aryloxy group comprising 1-20 carbon atoms; and each $R^2$, $R^4$, $R^5$, $R^6$, $R^7$, and $R^8$, independently comprises a hydrogen atom, an alkyl group, an alkenyl group, an aryl group, or a halogen atom; or wherein if $R^1$ comprises an —O—$R^9$, a —N—$R^9R^{10}$, a —B(OR$^{18}$)(OR$^{19}$) group, or a —SiR$^{20}_3$ group wherein $R^9$ comprises a hydrogen atom, an alkyl group, an alkenyl group, an aryl group, or a heteroatom-containing group comprising one or more oxygen, nitrogen, sulfur, or phosphorous atoms, and $R^{10}$ comprises a hydrogen atom, an alkyl group, an alkenyl group, an aryl group, or a heteroatom-containing group comprising one or more oxygen, nitrogen, sulfur, or phosphorous atoms, or $R^9$ and $R^{10}$ together with the atoms connecting form a heterocyclic ring structure, each $R^{18}$ and $R^{19}$ is independently a hydrogen atom, an alkyl group, an aryl group, or $R^{18}$ and $R^{19}$ together with the atoms connecting form a heterocyclic ring structure, each $R^{20}$ group is an alkyl group; and each $R^2$, $R^3$, $R^4$, $R^5$, $R^6$, $R^7$, and $R^8$, independently comprises a hydrogen atom, an alkyl group, an alkenyl group, an aryl group, or a halogen atom.

In some embodiments, the compositions comprise the structure of Formula II:

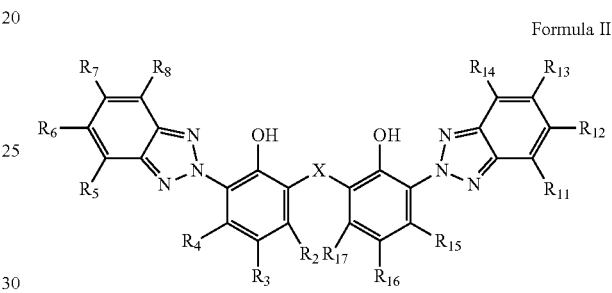

Formula II wherein X comprises an —O—, —NR$^{10}$—, —S(O)—, —S(O)$_2$—, or —S— linking group where $R^{10}$ comprises a hydrogen atom, an alkyl group, or an aryl group, each $R^2$, $R^3$, $R^4$, $R^5$, $R^6$, $R^7$, $R^8$, $R^{11}$, $R^{12}$, $R^{13}$, $R^{14}$, $R^{15}$, $R^{16}$, and $R^{17}$, independently comprises a hydrogen atom, an alkyl group, an alkenyl group, an aryl group, or a halogen atom.

Also disclosed are protected substituted or unsubstituted benzotriazole phenols comprising the general structure Formula III or Formula IV:

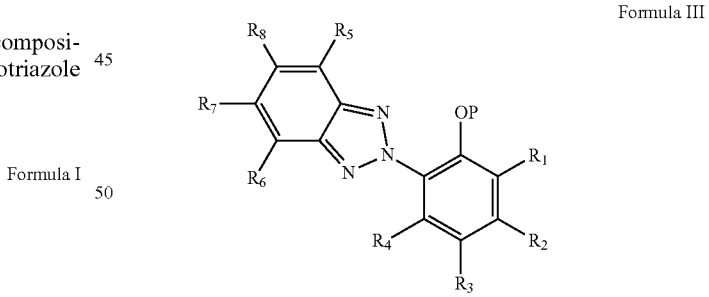

Formula III wherein the group P is a protective group comprising an alkyl, a substituted alkyl, or a silyl group;

and wherein if $R^1$ comprises a hydrogen atom; $R^3$ comprises an alkoxy or aryloxy group comprising 1-20 carbon atoms; and each $R^2$, $R^4$, $R^5$, $R^6$, $R^7$, and $R^8$, independently comprises a hydrogen atom, an alkyl group, an alkenyl group, an aryl group, or a halogen atom; or wherein if $R^1$ comprises an —O—$R^9$, a —N—$R^9R^{10}$, a —B(OR$^{18}$)(OR$^{19}$) group, or a —SiR$^{20}_3$ group wherein $R^9$ comprises a hydrogen atom, an alkyl group, an alkenyl group, an aryl group, or a heteroatom-containing group comprising one or more oxygen, nitrogen, sulfur, or phosphorous atoms, and $R^{10}$ comprises a hydrogen atom, an alkyl group, an alkenyl group, an aryl group, or a heteroatom-containing group comprising one or more oxygen, nitrogen, sulfur, or phosphorous atoms, or $R^9$ and $R^{10}$ together with the atoms connecting form a heterocyclic ring structure, each $R^8$ and $R^{19}$ is independently a hydrogen atom, an alkyl group, an aryl group, or $R^{18}$ and $R^{19}$ together with the atoms connecting form a heterocyclic ring structure, each $R^{20}$ group is an alkyl group; and each $R^2$, $R^3$, $R^4$, $R^5$, $R^6$, $R^7$, and $R^8$, independently comprises a hydrogen atom, an alkyl group, an alkenyl group, an aryl group, or a halogen atom; or Formula IV

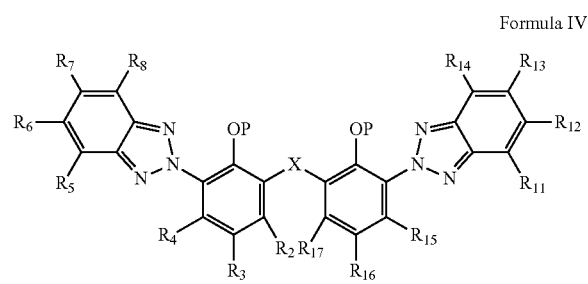

wherein the group P is a protective group comprising an alkyl, a substituted alkyl, or a silyl group; and wherein X comprises an —O—, —$NR^{10}$—, —S(O)—, —S(O)$_2$—, or —S— linking group where $R^{10}$ comprises a hydrogen atom, an alkyl group, or an aryl group, each $R^2$, $R^3$, $R^4$, $R^5$, $R^6$, $R^7$, $R^8$, $R^{11}$, $R^{12}$, $R^{13}$, $R^{14}$, $R^{15}$, $R^{16}$, and $R^{17}$, independently comprises a hydrogen atom, an alkyl group, an alkenyl group, an aryl group, or a halogen atom.

Also disclosed herein are methods of preparing substituted benzotriazole phenols comprising providing a protected phenolic compound of Formula III:

Formula III

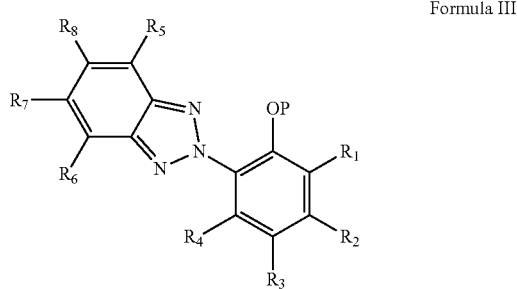

wherein the group P is a protective group comprising an alkyl, a substituted alkyl, or a silyl group; $R^1$ comprises a leaving group selected from a halogen atom, a triflate group, a tosylate group, or a sulfonate group; and each $R^2$, $R^3$, $R^4$, $R^5$, $R^6$, $R^7$, and $R^8$, independently comprises a hydrogen atom, an alkyl group, an alkenyl group, an aryl group, or a halogen atom; providing a compound with the general formula $R^{21}$—Z—X—H wherein $R^{21}$ comprises a hydrogen atom, an alkyl group, an alkenyl group, an aryl group, or a halogen atom; Z comprises an alkyl or aryl group, or a single bond; X comprises an —O—, —$NR^{10}$—, —S(O)—, —S(O)$_2$—, or —S— linking group where $R^{10}$ comprises a hydrogen atom, an alkyl group, or an aryl group; providing a palladium-based catalyst comprising at least one palladium-phosphine complex; providing at least one base; providing at least one solvent; mixing the protected phenolic compound of Formula III, the compound with the general formula $R^{21}$—Z—X—H, the palladium-based catalyst, the at least one base, and the at least one solvent to form a reaction mixture; and heating the reaction mixture to a temperature of at least 100° C. to effect a coupling reaction.

DETAILED DESCRIPTION

One class of useful phenolics are 2-(2-hydroxyphenyl) benzotriazoles or benzotriazole phenols. Benzotriazole phenols are an important class of UV absorbers, and in some cases, can absorb in the visible range as well. These compounds are often used as additives in materials, particularly polymeric materials, and can be used as synthons to prepare benzotriazole phenolate salts, which can also be useful as additives in materials, especially polymeric materials.

Disclosed herein are substituted benzotriazole phenols which have a range of properties and can be used to prepare benzotriazole phenolate salts. Additionally, protected substituted benzotriazole phenols, where the phenolic —OH group is protected, that is to say that it is an —OP group where P is the protective group, are also disclosed. Methods for preparing substituted benzotriazole phenols using coupling reactions are also disclosed.

The terms "a", "an", and "the" are used interchangeably with "at least one" to mean one or more of the elements being described.

The term "alkyl" refers to a monovalent group that is a radical of an alkane, which is a saturated hydrocarbon. The alkyl can be linear, branched, cyclic, or combinations thereof and typically has 1 to 20 carbon atoms. In some embodiments, the alkyl group contains 1 to 18, 1 to 12, 1 to 10, 1 to 8, 1 to 6, or 1 to 4 carbon atoms. Examples of alkyl groups include, but are not limited to, methyl, ethyl, n-propyl, isopropyl, n-butyl, isobutyl, tert-butyl (t-butyl), n-pentyl, n-hexyl, cyclohexyl, n-heptyl, n-octyl, and ethylhexyl.

The term "alkenyl" refers to a monovalent group that is a radical of an alkene, which is a hydrocarbon with at least one carbon-carbon double bond. The alkenyl can be linear, branched, cyclic, or combinations thereof and typically contains 2 to 20 carbon atoms. In some embodiments, the alkenyl contains 2 to 18, 2 to 12, 2 to 10, 4 to 10, 4 to 8, 2 to 8, 2 to 6, or 2 to 4 carbon atoms. Exemplary alkenyl groups include ethenyl, n-propenyl, and n-butenyl.

The term "heteroatom substituted" refers to an alkyl, aryl or other group which contains heteroatoms. These heteroatoms may be pendant atoms, for example, halogens or catenary atoms such as nitrogen, oxygen, boron, or sulfur.

The term "halogen" or "halogen atom" as used herein refers to fluorine, chlorine, bromine, or iodine.

The term "alkoxy" refers to a group with the general structure —O—R, where R is an alkyl group. The term "aryloxy" refers to a group with the general structure —O—R, where R is an aryl group. In some instances, the term alkoxy is used generically to describe both alkoxy and aryloxy groups.

The term "aryl" refers to an aromatic carbocyclic group that is a radical containing 1 to 5 rings which may be connected or fused. The aryl group may be substituted with alkyl or heteroalkyl groups. Examples of aryl groups include phenyl groups, naphthalene groups and anthracene groups.

The terms "room temperature" and "ambient temperature" are used interchangeably to mean temperatures in the range of 20° C. to 25° C.

The term "protective group" as used herein refers to a P portion of the general formula —OP, where O is an oxygen atom. The protective group is a reactive group which can be replaced with a hydrogen atom to form a hydroxyl group —OH, by a variety of techniques that are well understood in the art. Examples of protective groups are described below and in the Examples section.

Unless otherwise indicated, all numbers expressing feature sizes, amounts, and physical properties used in the specification and claims are to be understood as being modified in all instances by the term "about." Accordingly, unless indicated to the contrary, the numbers set forth are approximations that can vary depending upon the desired properties using the teachings disclosed herein.

The substituted benzotriazole phenols of this disclosure have the general structure shown in Formula I below:

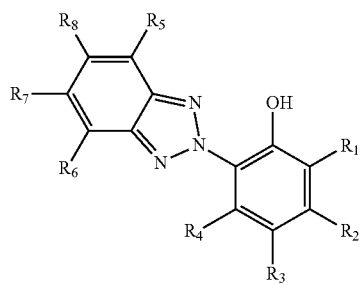

Formula I

In Formula I, at least one of $R^1$ and $R^3$ comprises a substituent group, that is to say a group other than a hydrogen atom. In many embodiments, both $R^1$ and $R^3$ comprise substituent groups. In some embodiments $R^1$ is not substituted i.e. $R^1$ comprises a hydrogen atom, in many other embodiments $R^1$ is a substituent group or another linked benzotriazole phenol group, as will described in greater detail below.

In embodiments where $R^1$ is not substituted (i.e. is a hydrogen atom), $R^3$ comprises an alkoxy or aryloxy group comprising 1-20 carbon atoms, and each $R^2$, $R^4$, $R^5$, $R^6$, $R^7$, and $R^8$, independently comprises a hydrogen atom, an alkyl group, an alkenyl group, an aryl group, or a halogen atom. In one embodiment, $R^1$ comprises a hydrogen atom, $R^3$ comprises an alkoxy group comprising 4 carbon atoms, and each $R^2$, $R^4$, $R^5$, $R^6$, $R^7$, and $R^8$, independently comprises a hydrogen atom.

In a wide variety of embodiments $R^1$ comprises a substituent group. In these embodiments, $R^1$ comprises a halogen atom, or a group comprising an —O—$R^9$, a —N—$R^9R^{10}$, a —B(O$R^{18}$)(O$R^{19}$), or a —Si$R^{20}_3$. In these embodiments $R^9$ comprises a hydrogen atom, an alkyl group, an alkenyl group, an aryl group, or a heteroatom-containing group comprising one or more oxygen, nitrogen, sulfur, or phosphorous atoms, and $R^{10}$ comprises a hydrogen atom, an alkyl group, an alkenyl group, an aryl group, or a heteroatom-containing group comprising one or more oxygen, nitrogen, sulfur, or phosphorous atoms, or $R^9$ and $R^{10}$ together with the atoms connecting form a heterocyclic ring structure, each $R^{18}$ and $R^{19}$ is independently a hydrogen atom, an alkyl group, an aryl group, or $R^{18}$ and $R^{19}$ together with the atoms connecting form a heterocyclic ring structure, each $R^{20}$ group is an alkyl group, and each $R^2$, $R^3$, $R^4$, $R^5$, $R^6$, $R^7$, and $R^8$, independently comprises a hydrogen atom, an alkyl group, an alkenyl group, an aryl group, or a halogen atom. Each of these embodiments will be described in greater detail below.

In some embodiments, $R^1$ comprises a relatively small substituent group, one which is of smaller molecular weight and/or steric size relative to the benzotriazole phenol base molecule. In other embodiments, the $R^1$ group is a substituent group that is comparable in size and/or steric size to the benzotriazole phenol base molecule, and is in fact another benzotriazole phenol linked to the benzotriazole phenol base molecule by an oxygen, nitrogen-based, or sulfur-based linking group. Examples of the first type, where $R^1$ comprises a relatively small substituent group, will be presented first.

In some embodiments, $R^1$ comprises a halogen atom. Suitable halogen atoms include fluorine, bromine, chlorine and iodine. Bromine (Br) and chlorine (Cl) are particularly suitable.

In some embodiments, where $R^1$ comprises an —O—$R^9$ group wherein $R^9$ comprises
an alkyl group with 1-20 carbon atoms, or an aryl group. In many of these embodiments, $R^3$ is also a substituent group, typically $R^3$ is an alkyl group with 1-20 carbon atoms.

In some embodiments, $R^9$ comprises an alkyl group with 1-6 carbon atoms, in one particular embodiment $R^9$ comprises an alkyl group with 4 carbon atoms, and $R^3$ is an alkyl group with 8 carbon atoms, typically an iso-octyl group.

In other embodiments, $R^9$ comprises an aryl group comprising a substituted phenyl group. In some particular embodiments, $R^9$ comprises a 3-methyl phenyl group or a 4-methyl phenyl group, and $R^3$ is an alkyl group with 8 carbon atoms, typically an iso-octyl group.

In another group of embodiments, $R^1$ comprises an —N—$R^9R^{10}$ group. In some of these embodiments, $R^9$ comprises a hydrogen atom, an alkyl group with 1-20 carbon atoms, or an aryl group. In these embodiments, $R^{10}$ independently comprises a hydrogen atom or alkyl group with 1-6 carbon atoms. In many of these embodiments, $R^3$ is also a substituent group, typically $R^3$ is an alkyl group with 1-20 carbon atoms.

In one embodiment, both $R^9$ and $R^{10}$ comprise a hydrogen atom. In other embodiments, $R^9$ comprises an alkyl group with 1-6 carbon atoms, or an aryl group comprising a 4-alkyl substituted phenyl group, wherein the alkyl substituted group has 1-6 carbon atoms, and $R^{10}$ comprises a hydrogen atom.

In one particular embodiment, $R^9$ comprises an alkyl group with 1 carbon atom (a methyl group), $R^{10}$ comprises a hydrogen atom, and $R^3$ is an alkyl group with 8 carbon atoms, typically an iso-octyl group. In one particular embodiment, $R^9$ comprises an alkyl group with 6 carbon atoms, $R^{10}$ comprises a hydrogen atom, and $R^3$ is an alkyl group with 8 carbon atoms, typically an iso-octyl group. In yet another particular embodiment, $R^9$ comprises a 4-alkyl substituted phenyl group, wherein the alkyl substituent group has 6 carbon atoms (i.e. the group comprises a 4-hexyl phenyl group), $R^{10}$ comprises a hydrogen atom, and $R^3$ is an alkyl group with 8 carbon atoms, typically an iso-octyl group.

In another particular embodiment, $R^1$ comprises a —B(OH)$_2$ group, in other embodiments $R^1$ comprises —B(—O—C(Me)$_2$-C(Me)$_2$-O—), and $R^3$ is an alkyl group with 8 carbon atoms, typically an iso-octyl group.

In another particular embodiment, $R^1$ comprises a —Si$R^{20}_3$ group where $R^{20}$ comprises an alkyl group with 1-6 carbon atoms, in some embodiments $R^{20}$ comprises 3 carbon atoms, typically $R^{20}$ comprises an isopropyl group.

As mentioned above, in other embodiments the $R^1$ group is a substituent group that is comparable in size and/or steric size to the benzotriazole phenol base molecule, and is in fact another benzotriazole phenol linked to the benzotriazole phenol base molecule by an oxygen, nitrogen-based, or sulfur-based linking group. Examples of this second type of compound are described by Formula II below:

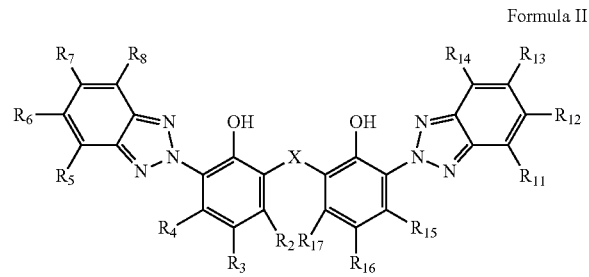

Formula II where the $R^1$ group is an —X—$R^9$ group an X is a linking group comprising an —O—, —$NR^{10}$—, —S(O)—, or —S—, where S(O) is a sulfinyl group S=O, and where $R^{10}$ comprises a hydrogen atom, an alkyl group, or an aryl group. The $R^9$ group in these embodiments is another benzotriazole phenol group, which may be the same or different from the base benzotriazole phenol group. In these embodiments, each $R^2$, $R^3$, $R^4$, $R^5$, $R^6$, $R^7$, $R^8$, $R^{11}$, $R^{12}$, $R^{13}$, $R^{14}$, $R^{15}$, $R^{16}$, and $R^{17}$, independently comprises a hydrogen atom, an alkyl group, an alkenyl group, an aryl group, or a halogen atom.

In some embodiments of the compounds of Formula II, X comprises an —$NR^{10}$— linking group where $R^{10}$ comprises a hydrogen atom, or an alkyl group comprising 1-3 carbon atoms. Typically in these embodiments, the $R^3$ and $R^{16}$ groups are substituent groups, where $R^3$ and $R^{16}$ each comprise an alkyl group with 1-20 carbon atoms. Typically, each $R^2$, $R^4$, $R^5$, $R^6$, $R^7$, $R^8$, $R^{11}$, $R^{12}$, $R^{13}$, $R^{14}$, $R^{15}$, and $R^{17}$, is a hydrogen atom.

In one particular embodiment, X comprises an —$NR^{10}$— linking group where $R^{10}$ comprises a hydrogen atom, the $R^3$ and $R^{16}$ groups are alkyl groups with 8 carbon atoms, typically iso-octyl groups, and each $R^2$, $R^4$, $R^5$, $R^6$, $R^7$, $R^8$, $R^{11}$, $R^{12}$, $R^{13}$, $R^{14}$, $R^{15}$, and $R^{17}$, is a hydrogen atom.

In another particular embodiment, X comprises an —$NR^{10}$— linking group where $R^{10}$ comprises an alkyl group with 1 carbon atom (a methyl group), the $R^3$ and $R^{16}$ groups are alkyl groups with 8 carbon atoms, typically iso-octyl groups, and each $R^2$, $R^4$, $R^5$, $R^6$, $R^7$, $R^8$, $R^{11}$, $R^{12}$, $R^{13}$, $R^{14}$, $R^{15}$, and $R^{17}$, is a hydrogen atom.

In some embodiments of the compounds of Formula II, X comprises an —O— linking group. Typically in these embodiments, the $R^3$ and $R^{16}$ groups are substituent groups, where $R^3$ and $R^{16}$ each comprise an alkyl group with 1-20 carbon atoms. Typically, each $R^2$, $R^4$, $R^5$, $R^6$, $R^7$, $R^8$, $R^{11}$, $R^{12}$, $R^{13}$, $R^{14}$, $R^{15}$, and $R^{17}$, is a hydrogen atom.

In one particular embodiment, X comprises an —O— linking group, the $R^3$ and $R^{16}$ groups are alkyl groups with 8 carbon atoms, typically iso-octyl groups, and each $R^2$, $R^4$, $R^5$, $R^6$, $R^7$, $R^8$, $R^{11}$, $R^{12}$, $R^{13}$, $R^{14}$, $R^{15}$, and $R^{17}$, is a hydrogen atom.

In some embodiments of the compounds of Formula II, X comprises a —S(O)— linking group. Typically in these embodiments, the $R^3$ and $R^{16}$ groups are substituent groups, where $R^3$ and $R^{16}$ each comprise an alkyl group with 1-20 carbon atoms. Typically, each $R^2$, $R^4$, $R^5$, $R^6$, $R^7$, $R^8$, $R^{11}$, $R^{12}$, $R^{13}$, $R^{14}$, $R^{15}$, and $R^{17}$, is a hydrogen atom.

In one particular embodiment, X comprises a —S(O)— linking group, the $R^3$ and $R^{16}$ groups are alkyl groups with 8 carbon atoms, typically iso-octyl groups, and each $R^2$, $R^4$, $R^5$, $R^6$, $R^7$, $R^8$, $R^{11}$, $R^{12}$, $R^{13}$, $R^{14}$, $R^{15}$, and $R^{17}$, is a hydrogen atom.

In some embodiments of the compounds of Formula II, X comprises a —S— linking group. Typically in these embodiments, the $R^3$ and $R^{16}$ groups are substituent groups, where $R^3$ and $R^{16}$ each comprise an alkyl group with 1-20 carbon atoms. Typically, each $R^2$, $R^4$, $R^5$, $R^6$, $R^7$, $R^8$, $R^{11}$, $R^{12}$, $R^{13}$, $R^{14}$, $R^{15}$, and $R^{17}$, is a hydrogen atom.

In one particular embodiment, X comprises a —S— linking group, the $R^3$ and $R^{16}$ groups are alkyl groups with 8 carbon atoms, typically iso-octyl groups, and each $R^2$, $R^4$, $R^5$, $R^6$, $R^7$, $R^8$, $R^{11}$, $R^{12}$, $R^{13}$, $R^{14}$, $R^{15}$, and $R^{17}$, is a hydrogen atom.

Also disclosed herein are a series of protected benzotriazole phenols. These compounds are ones in which the hydrogen atom of the phenol hydroxyl group (—OH) is replaced by a protective group (—OP). Typically these protective groups are alkyl, substituted alkyl, or silyl groups. Typically the protected benzotriazole phenols are isolated as intermediates in the preparation of the phenols. The protective groups (P) can be removed to generate the hydroxyl group and prepare the phenol.

The use of protective groups to protect the reactive phenol hydroxyl group is well understood in the art. Protective groups can be used to protect the phenol hydroxyl group during chemical synthesis so as to prevent side reactions with the reactive phenol hydroxyl group. Additionally, it can sometimes be desirable to isolate the protected benzotriazole phenol and convert it to the desired phenol prior to use.

Corresponding protected benzotriazole phenol compounds can be prepared and/or isolated for virtually all of the above described benzotriazole phenol compounds. These compounds can be described by the general formulas Formula III and Formula IV below:

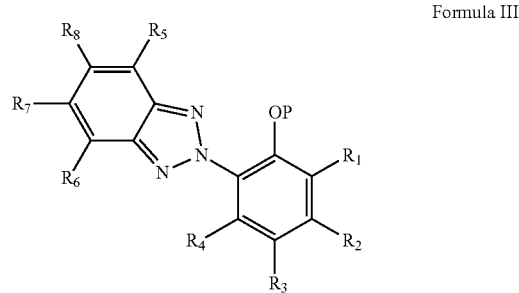

Formula III

In Formula III, at least one of $R^1$ and $R^3$ comprises a substituent group, that is to say a group other than a hydrogen atom. In many embodiments, both $R^1$ and $R^3$ comprise substituent groups. In some embodiments $R^1$ is not substituted i.e. $R^1$ comprises a hydrogen atom, in many other embodiments $R^1$ is a substituent group or another linked benzotriazole phenol group, as will described in greater detail below.

In Formula III, the group P is a protective group. Typically the protective group comprises an alkyl, a substituted alkyl, or a silyl group. In some embodiments P comprises an alkyl group, typically a methyl group. In other embodiments, P comprises a substituted alkyl group, such as an —$CH_2OCH_3$ group. In yet other embodiments, P comprises a silyl group such as —$Si((i-Pr)_3$, where i-Pr is an iso-propyl group.

In embodiments where $R^1$ is not substituted (i.e. is a hydrogen atom), $R^3$ comprises an alkoxy or aryloxy group comprising 1-20 carbon atoms, and each $R^2$, $R^4$, $R^5$, $R^6$, $R^7$, and $R^8$, independently comprises a hydrogen atom, an alkyl group, an alkenyl group, an aryl group, or a halogen atom. In one embodiment, $R^1$ comprises a hydrogen atom, $R^3$ comprises an alkoxy group comprising 4 carbon atoms, and each $R^2$, $R^4$, $R^5$, $R^6$, $R^7$, and $R^8$, independently comprises a hydrogen atom.

In a wide variety of embodiments $R^1$ comprises a substituent group. In these embodiments, $R^1$ comprises a halogen atom, or a group comprising an —O—$R^9$, a —N—$R^9R^{10}$, a —B($OR^{18}$)($OR^{19}$), or a —Si$R^{20}{}_3$. In these embodiments $R^9$ comprises a hydrogen atom, an alkyl group, an alkenyl group, an aryl group, or a heteroatom-containing group comprising one or more oxygen, nitrogen, sulfur, or phosphorous atoms, and $R^{10}$ comprises a hydrogen atom, an alkyl group, an alkenyl group, an aryl group, or a heteroatom-containing group comprising one or more oxygen, nitrogen, sulfur, or phosphorous atoms, or $R^9$ and $R^{10}$ together with the atoms connecting form a heterocyclic ring structure, each $R^{18}$ and $R^{19}$ is independently a hydrogen atom, an alkyl group, an aryl group, or $R^{18}$ and $R^{19}$ together with the atoms connecting form a heterocyclic ring structure, each $R^{20}$ group is an alkyl group, and each $R^2$, $R^3$, $R^4$, $R^5$, $R^6$, $R^7$, and $R^8$, independently comprises a hydrogen atom, an alkyl group, an alkenyl group, an aryl group, or a halogen atom. Each of these embodiments will be described in greater detail below.

In some embodiments, $R^1$ comprises a relatively small substituent group, one which is of smaller molecular weight and/or steric size relative to the benzotriazole phenol base molecule. In other embodiments, the $R^1$ group is a substituent group that is comparable in size and/or steric size to the benzotriazole phenol base molecule, and is in fact another benzotriazole phenol linked to the benzotriazole phenol base molecule by an oxygen or nitrogen-based linking group. Examples of the first type, where $R^1$ comprises a relatively small substituent group, will be presented first.

In some embodiments, $R^1$ comprises a halogen atom. Suitable halogen atoms include fluorine, bromine, chlorine and iodine. Bromine (Br) and chlorine (Cl) are particularly suitable.

In some embodiments, where $R^1$ comprises an —O—$R^9$ group wherein $R^9$ comprises
an alkyl group with 1-20 carbon atoms, or an aryl group. In many of these embodiments, $R^3$ is also a substituent group, typically $R^3$ is an alkyl group with 1-20 carbon atoms.

In some embodiments, $R^9$ comprises an alkyl group with 1-6 carbon atoms, in one particular embodiment $R^9$ comprises an alkyl group with 4 carbon atoms, and $R^3$ is an alkyl group with 8 carbon atoms, typically an iso-octyl group.

In other embodiments, $R^9$ comprises an aryl group comprising a substituted phenyl group. In some particular embodiments, $R^9$ comprises a 3-methyl phenyl group or a 4-methyl phenyl group, and $R^3$ is an alkyl group with 8 carbon atoms, typically an iso-octyl group.

In another group of embodiments, $R^1$ comprises an —N—$R^9R^{10}$ group. In some of these embodiments, $R^9$ comprises an alkyl group with 1-20 carbon atoms, or an aryl group. In these embodiments, $R^{10}$ independently comprises a hydrogen atom or alkyl group with 1-6 carbon atoms. In many of these embodiments, $R^3$ is also a substituent group, typically $R^3$ is an alkyl group with 1-20 carbon atoms.

In some embodiments, $R^9$ comprises an alkyl group with 1-6 carbon atoms, or an aryl group comprising a 3-alkyl substituted phenyl group, wherein the alkyl substituted group has 1-6 carbon atoms, and $R^{10}$ comprises a hydrogen atom.

In one particular embodiment, $R^9$ comprises an alkyl group with 1 carbon atom (a methyl group), $R^{10}$ comprises a hydrogen atom, and $R^3$ is an alkyl group with 8 carbon atoms, typically an iso-octyl group. In one particular embodiment, $R^9$ comprises an alkyl group with 6 carbon atoms, $R^{10}$ comprises a hydrogen atom, and $R^3$ is an alkyl group with 8 carbon atoms, typically an iso-octyl group. In yet another particular embodiment, $R^9$ comprises a 4-alkyl substituted phenyl group, wherein the alkyl substituted group has 6 carbon atoms (i.e. the group comprises a 4-hexyl phenyl group), $R^{10}$ comprises a hydrogen atom, and $R^3$ is an alkyl group with 8 carbon atoms, typically an iso-octyl group.

In another particular embodiment, $R^1$ comprises a —B(OH)$_2$ group, in other embodiments $R^1$ comprises —B(—O—C(Me)$_2$-C(Me)$_2$-O—), and $R^3$ is an alkyl group with 8 carbon atoms, typically an iso-octyl group.

In another particular embodiment, $R^1$ comprises a —Si$R^{20}{}_3$ group where $R^{20}$ comprises an alkyl group with 1-6 carbon atoms, in some embodiments $R^{20}$ comprises 3 carbon atoms, typically $R^{20}$ comprises an isopropyl group.

As mentioned above, in other embodiments the $R^1$ group is a substituent group that is comparable in size and/or steric size to the benzotriazole phenol base molecule, and is in fact another benzotriazole phenol linked to the benzotriazole phenol base molecule by an oxygen, nitrogen-based, or sulfur-based linking group. Examples of this second type of compound are described by Formula II below:

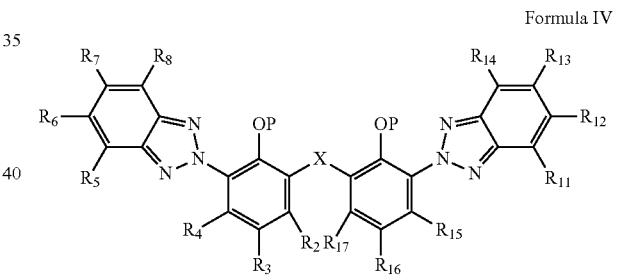

Formula IV where the $R^1$ group is an —X—$R^9$ group an X is a linking group comprising an —O—, —$NR^{10}$—, —S(O)—, or —S—, where S(O) is a sulfinyl group S=O, S(O)$_2$ is a sulfonyl group O=S=O, and where $R^{10}$ comprises a hydrogen atom, an alkyl group, or an aryl group. The $R^9$ group in these embodiments is another benzotriazole phenol group, which may be the same or different from the base benzotriazole phenol group. In these embodiments, each $R^2$, $R^3$, $R^4$, $R^5$, $R^6$, $R^7$, $R^8$, $R^{11}$, $R^{12}$, $R^{13}$, $R^{14}$, $R^{15}$, $R^{16}$, and $R^{17}$, independently comprises a hydrogen atom, an alkyl group, an alkenyl group, an aryl group, or a halogen atom.

In Formula IV, the group P is a protective group. Typically the protective group comprises an alkyl, a substituted alkyl, or a silyl group. In some embodiments P comprises an alkyl group, typically a methyl group. In other embodiments, P comprises a substituted alkyl group, such as an —CH$_2$OCH$_3$ group. In yet other embodiments, P comprises a silyl group such as —Si((i-Pr)$_3$, where i-Pr is an iso-propyl group.

In some embodiments of the compounds of Formula IV, X comprises an —$NR^{10}$— linking group where $R^{10}$ comprises a hydrogen atom, or an alkyl group comprising 1-3 carbon atoms. Typically in these embodiments, the $R^3$ and $R^{16}$ groups are substituent groups, where $R^3$ and $R^{16}$ each comprise an alkyl group with 1-20 carbon atoms. Typically, each $R^2$, $R^4$, $R^5$, $R^6$, $R^7$, $R^8$, $R^{11}$, $R^{12}$, $R^{13}$, $R^{14}$, $R^{15}$, and $R^{17}$, is a hydrogen atom.

In one particular embodiment, X comprises an —$NR^{10}$— linking group where $R^{10}$ comprises a hydrogen atom, the $R^3$ and $R^{16}$ groups are alkyl groups with 8 carbon atoms, typically iso-octyl groups, and each $R^2$, $R^4$, $R^5$, $R^6$, $R^7$, $R^8$, $R^{11}$, $R^{12}$, $R^{13}$, $R^{14}$, $R^{15}$, and $R^{17}$, is a hydrogen atom.

In another particular embodiment, X comprises an —$NR^{10}$— linking group where $R^{10}$ comprises an alkyl group with 1 carbon atom (a methyl group), the $R^3$ and $R^{16}$ groups are alkyl groups with 8 carbon atoms, typically iso-octyl groups, and each $R^2$, $R^4$, $R^5$, $R^6$, $R^7$, $R^8$, $R^{11}$, $R^{12}$, $R^{13}$, $R^{14}$, $R^{15}$, and $R^{17}$, is a hydrogen atom.

In some embodiments of the compounds of Formula IV, X comprises an —O— linking group. Typically in these embodiments, the $R^3$ and $R^{16}$ groups are substituent groups, where $R^3$ and $R^{16}$ each comprise an alkyl group with 1-20 carbon atoms. Typically, each $R^2$, $R^4$, $R^5$, $R^6$, $R^7$, $R^8$, $R^{11}$, $R^{12}$, $R^{13}$, $R^{14}$, $R^{15}$, and $R^{17}$, is a hydrogen atom.

In one particular embodiment, X comprises an —O— linking group, the $R^3$ and $R^{16}$ groups are alkyl groups with 8 carbon atoms, typically iso-octyl groups, and each $R^2$, $R^4$, $R^5$, $R^6$, $R^7$, $R^8$, $R^{11}$, $R^{12}$, $R^{13}$, $R^{14}$, $R^{15}$, and $R^{17}$, is a hydrogen atom.

In some embodiments of the compounds of Formula IV, X comprises a —S(O)— linking group. Typically in these embodiments, the $R^3$ and $R^{16}$ groups are substituent groups, where $R^3$ and $R^{16}$ each comprise an alkyl group with 1-20 carbon atoms. Typically, each $R^2$, $R^4$, $R^5$, $R^6$, $R^7$, $R^8$, $R^{11}$, $R^{12}$, $R^{13}$, $R^{14}$, $R^{15}$, and $R^{17}$, is a hydrogen atom.

In one particular embodiment, X comprises a —S(O)— linking group, the $R^3$ and $R^{16}$ groups are alkyl groups with 8 carbon atoms, typically iso-octyl groups, and each $R^2$, $R^4$, $R^5$, $R^6$, $R^7$, $R^8$, $R^{11}$, $R^{12}$, $R^{13}$, $R^{14}$, $R^{15}$, and $R^{17}$, is a hydrogen atom.

In some embodiments of the compounds of Formula IV, X comprises a —$S(O)_2$— linking group. Typically in these embodiments, the $R^3$ and $R^{16}$ groups are substituent groups, where $R^3$ and $R^{16}$ each comprise an alkyl group with 1-20 carbon atoms. Typically, each $R^2$, $R^4$, $R^5$, $R^6$, $R^7$, $R^8$, $R^{11}$, $R^{12}$, $R^{13}$, $R^{14}$, $R^{15}$, and $R^{17}$, is a hydrogen atom.

In one particular embodiment, X comprises a —$S(O)_2$— linking group, the $R^3$ and $R^{16}$ groups are alkyl groups with 8 carbon atoms, typically iso-octyl groups, and each $R^2$, $R^4$, $R^5$, $R^6$, $R^7$, $R^8$, $R^{11}$, $R^{12}$, $R^{13}$, $R^{14}$, $R^{15}$, and $R^{17}$, is a hydrogen atom.

In some embodiments of the compounds of Formula IV, X comprises a —S— linking group. Typically in these embodiments, the $R^3$ and $R^{16}$ groups are substituent groups, where $R^3$ and $R^{16}$ each comprise an alkyl group with 1-20 carbon atoms. Typically, each $R^2$, $R^4$, $R^5$, $R^6$, $R^7$, $R^8$, $R^{11}$, $R^{12}$, $R^{13}$, $R^{14}$, $R^{15}$, and $R^{17}$, is a hydrogen atom.

In one particular embodiment, X comprises a —S— linking group, the $R^3$ and $R^{16}$ groups are alkyl groups with 8 carbon atoms, typically iso-octyl groups, and each $R^2$, $R^4$, $R^5$, $R^6$, $R^7$, $R^8$, $R^{11}$, $R^{12}$, $R^{13}$, $R^{14}$, $R^{15}$, and $R^{17}$, is a hydrogen atom.

Also disclosed herein are methods for preparing substituted benzotriazole phenol compounds via coupling reactions. Cross-coupling reactions have been studied and used for many years. Carbon-carbon bond formation is the most studied form of cross-coupling, while non-carbon nucleophilic coupling partners were not discovered until the 1990's. Buchwald and Hartwig have made tremendous advances with carbon-heteroatom coupling, however the scope can still be quite limited, especially with hindered and/or deactivated substrates. Benzotriazole phenols are a particularly challenging substrate for cross-coupling due to the sterically hindered hydroxyl substituent located ortho to the halide and also due to the chelating effect of the benzotriazole group, leading to deactivation of the metal catalyst.

Disclosed herein are the first examples of utilizing a cross-coupling method to install a heteroatom in the ortho position of a benzotriazole. In addition, no cross-coupling has been used to synthesize a bis-benzotriazole phenol with a heteroatom linking group.

The method comprises preparing a reaction mixture that includes not only the reactants described in detail below, but also at least one solvent, at least one base, and at least one palladium-based catalyst. This reaction mixture is heated to a temperature of at least 100° C. to effect the coupling reaction.

The methods for preparing substituted benzotriazole phenols comprise providing a protected phenolic compound of Formula III:

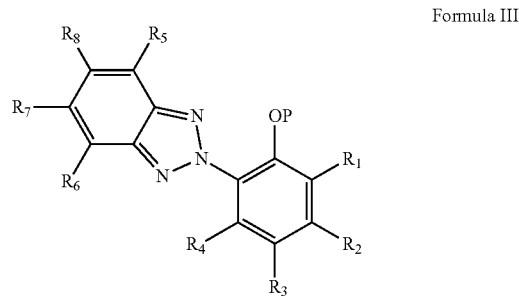

Formula III where the group P is a protective group comprising an alkyl, a substituted alkyl, or a silyl group; $R^1$ comprises a leaving group selected from a halogen atom, a triflate group, a tosylate group, or a sulfonate group; and each $R^2$, $R^3$, $R^4$, $R^5$, $R^6$, $R^7$, and $R^8$, independently comprises a hydrogen atom, an alkyl group, an alkenyl group, an aryl group, or a halogen atom; providing a compound with the general formula $R^{21}$—Z—X—H wherein $R^{21}$ comprises a hydrogen atom, an alkyl group, an alkenyl group, an aryl group, or a halogen atom; Z comprises an alkyl or aryl group, or a single bond; X comprises an —O—, —$NR^{10}$—, —S(O)—, or —S— linking group where $R^{10}$ comprises a hydrogen atom, an alkyl group, or an aryl group; providing a palladium-based catalyst comprising at least one palladium-phosphine complex; providing at least one base; providing at least one solvent; mixing the protected phenolic compound of Formula III, the compound with the general formula $R^{21}$—Z—X—H, the palladium-based catalyst, the at least one base, and the at least one solvent; and permitting them to react in a coupling reaction. The P group is then removed to replace the —OP group with an —OH group to form the phenol functionality, resulting in the substituted benzotriazole phenols described above.

In some embodiments, the P group is an alkyl group of silyl group. In some specific embodiments, the P group is a methyl group or a tri-alkyl silyl group.

Any suitable group can be used as the leaving group $R^1$. In some embodiments, the leaving group $R^1$ comprises a halogen atom. Bromine atoms are particularly suitable leaving groups, but other halogens, especially chlorine, may also be suitable.

Each $R^2$, $R^3$, $R^4$, $R^5$, $R^6$, $R^7$, and $R^8$, independently comprises a hydrogen atom, an alkyl group, an alkenyl group, an aryl group, or a halogen atom. Typically at least one of these groups comprises a substituent group, meaning that it is an atom or group other than a hydrogen atom. In some embodiments, each $R^2$, $R^4$, $R^5$, $R^6$, $R^7$, and $R^8$ group is a hydrogen atom, and the group $R^3$ comprises a substituent group, typically an alkyl group. In some specific embodiments, $R^3$ comprises an alkyl group with 8 carbon atoms, typically an iso-octyl group.

A wide variety of compounds with the general formula $R^{21}$—Z—X—H can be used to couple with the compound of Formula III. In some embodiments, the compound with the general formula $R^{21}$—Z—X—H is a relatively simple compound, whereas in other embodiments, the compound with the general formula $R^{21}$—Z—X—H is similar in structure and complexity to the compound of Formula III.

Examples of relatively simple compounds with the general formula $R^{21}$—Z—X—H are those where X is —O—, and the $R^{21}$—Z— group comprises an alkyl group, or a substituted aromatic group. In these embodiments, the $R^{21}$—Z—X—H compounds are alcohols or phenols. Examples of such $R^{21}$—Z—X—H compounds are $H_3C$—$CH_2$—$CH_2$—$CH_2$—OH (n-butanol) in which $R^{21}$ is a hydrogen atom, Z is —$H_2C$—$CH_2$—$CH_2$—$CH_2$— group, and X is —O—. Other examples are ones in which $R^{21}$—Z— is a substituted aromatic ring, so that the $R^{21}$—Z—X—H compound is a substituted phenol such as 3-methyl phenol or 4-methyl phenol.

Other examples of relatively simple compounds with the general formula $R^{21}$—Z—X—H are those where X is —$NR^{10}$—, where $R^{10}$ comprises a hydrogen atom, an alkyl group, or an aryl group, and the $R^{21}$—Z— group comprises an alkyl group, or a substituted aromatic group. Examples of such $R^{21}$—Z—X—H compounds are $H_3C$—$NH_2$ (methyl amine) in which $R^{21}$ is a hydrogen atom, Z is a —$CH_2$— group, and X is —$NR^{10}$—, where $R^{10}$ comprises a hydrogen atom and $H_3C$—$H_2C$—$CH_2$—$CH_2$—$CH_2$—$CH_2$—$NH_2$ (hexyl amine) in which $R^{21}$ is a hydrogen atom, Z is a —$H_2C$—$CH_2$—$CH_2$—$CH_2$—$CH_2$— group, and X is —$NR^{10}$—, where $R^{10}$ comprises a hydrogen atom. Other examples are ones in which $R^{21}$—Z— is a substituted aromatic ring, so that the $R^{21}$—Z—X—H compound is a substituted aniline such as 4-hexyl aniline.

The methods of this disclosure also include embodiments where the compound with the general formula $R^{21}$—Z—X—H comprises a more complex structure, being described by Formula IIIa:

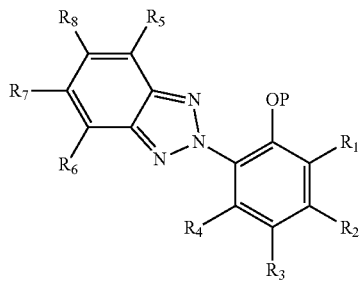

Formula IIIa where $R^1$ comprises the group —XH, where X comprises an —O—, —$NR^{10}$—, —S(O)—, or —S— linking group where $R^{10}$ comprises a hydrogen atom, an alkyl group, or an aryl group; the group P is a protective group comprising an alkyl, a substituted alkyl, or a silyl group; and each $R^2$, $R^3$, $R^4$, $R^5$, $R^6$, $R^7$, and $R^8$, independently comprises a hydrogen atom, an alkyl group, an alkenyl group, an aryl group, or a halogen atom.

In some embodiments, the P group is an alkyl group of silyl group. In some specific embodiments, the P group is a methyl group or a tri-alkyl silyl group.

Each $R^2$, $R^3$, $R^4$, $R^5$, $R^6$, $R^7$, and $R^8$, independently comprises a hydrogen atom, an alkyl group, an alkenyl group, an aryl group, or a halogen atom. Typically at least one of these groups comprises a substituent group, meaning that it is an atom or group other than a hydrogen atom. In some embodiments, each $R^2$, $R^4$, $R^5$, $R^6$, $R^7$, and $R^8$ group is a hydrogen atom, and the group $R^3$ comprises a substituent group, typically an alkyl group. In some specific embodiments, $R^3$ comprises an alkyl group with 8 carbon atoms, typically an iso-octyl group. In some specific embodiments, X comprises an —O—, —$NR^{10}$—, —S(O)—, or —S— linking group where $R^{10}$ comprises a hydrogen atom or a methyl group.

In an alternative embodiment of the method of this disclosure, the compound with the general formula $R^{21}$—Z—XH comprises $NH_3$, and the coupling reaction comprises a second coupling reaction to form a compound of Formula IV:

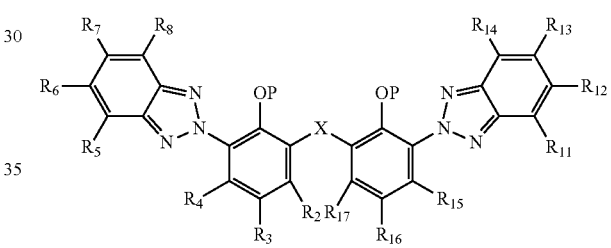

Formula IV where the group P is a protective group comprising an alkyl, a substituted alkyl, or a silyl group; and X comprises an —$NR^{10}$— linking group where $R^{10}$ comprises a hydrogen atom, each $R^2$, $R^3$, $R^4$, $R^5$, $R^6$, $R^7$, $R^8$, $R^1$, $R^{12}$, $R^{13}$, $R^{14}$, $R^{15}$, $R^{16}$, and $R^{17}$, independently comprises a hydrogen atom, an alkyl group, an alkenyl group, an aryl group, or a halogen atom. In this coupling reaction, two compounds of Formula III are linked via a —NH— linking group.

Each $R^2$, $R^3$, $R^4$, $R^5$, $R^6$, $R^7$, $R^8$, $R^{11}$, $R^{12}$, $R^{13}$, $R^{14}$, $R^{15}$, $R^{16}$, and $R^{17}$, independently comprises a hydrogen atom, an alkyl group, an alkenyl group, an aryl group, or a halogen atom. Typically at least two of these groups comprises a substituent group, meaning that it is an atom or group other than a hydrogen atom. In some embodiments, each $R^2$, $R^4$, $R^5$, $R^6$, $R^7$, $R^8$, $R^{11}$, $R^{12}$, $R^{13}$, $R^{14}$, $R^{15}$, and $R^{17}$ group is a hydrogen atom, and the groups $R^3$ and $R^{16}$ comprise substituent groups, typically alkyl groups. In some specific embodiments, $R^3$ and $R^{16}$ comprise alkyl groups with 8 carbon atoms, typically iso-octyl groups.

As to the other components of the reaction mixture, the at least one solvent, the at least one base and the at least one palladium-based catalyst, a wide variety of suitable materials are useful. Examples of suitable solvents include: hydrocarbon solvents such as hexane, heptane, toluene or benzene; ethers such as dioxane or THF (tetrahydrofuran); halogenated solvents such as dichloromethane or chloroform; and acetates such as ethylacetate; aqueous solvents including water or water and one or more water miscible solvent such as an alcohol (such as tert-butanol); and mixtures thereof. Examples of suitable bases include a wide array of inorganic or organic bases including: metal hydroxides or alkoxides such as sodium hydroxide, potassium hydroxide, sodium ethoxide, or sodium tert-butoxide; metal carbonates and phosphates such as potassium carbonate or cesium carbonate, or potassium phosphate; lithium salts such as n-butyl lithium, or lithium hexamethyldisilazane; sodium hydride; organic amine bases such as triethyl amine; and the like. The palladium-based catalysts comprise palladium-phosphine complexes. The palladium-phosphine complexes are typically generated in situ by the combination of a palladium-based precatalyst and at least one phosphine ligand. Examples of suitable palladium-based precatalysts and suitable phosphine ligands are described in greater detail in the Examples section. Particularly suitable palladium-based precatalysts include: palladium acetate; allyl palladium chloride; and tris(dibenzylideneacetone)dipalladium. Particularly suitable phosphine ligands include: 2-(Dicyclohexylphosphino)-2',4',6'-tri-i-propyl-1,1'-biphenyl (XPhos); 2-(Di-t-butylphosphino)-3-methoxy-6-methyl-2'-4'-6'-tri-i-propyl-1,1'-biphenyl (RockPhos); and 2-(Di-t-butylphosphino)-3,6-dimethoxy-2',4',6'-tri-i-propyl-1,1'-biphenyl (t-buBrettPhos) all available from Strem.

The compounds formed in the coupling reactions contain protected phenolic groups (that is to say groups —OP). After the coupling reactions are carried out, the protecting groups P can be removed and replaced by a hydrogen atom to form the phenol functionality according to well understood deprotection reactions to form the substituted benzotriazole phenol compounds of this disclosure.

Descriptions for the preparation of each of these substituted benzotriazole phenol compounds is described in detail in the Examples section below.

EXAMPLES

These examples are merely for illustrative purposes only and are not meant to be limiting on the scope of the appended claims. All parts, percentages, ratios, etc. in the examples and the rest of the specification are by weight, unless noted otherwise. Solvents were Alfa Aesar (Chem-Seal grade) and were used with no further purification. Solvents that were used in separations, isolations, chromatography, and other general use were obtained from EMD (Omnisolv Grade).

The following abbreviations are used throughout the Examples: M=molar; min=minutes; h=hours; equiv=equivalents; x=times; g=grams; mg=milligrams; mmol=millimoles; L=liters; mL=milliliters; rt=room temperature; aq=aqueous;

Materials

The following is a table of commercially available materials and reagents that were used.

| Compound | Supplier |
| --- | --- |
| Bases | |
| sodium ethoxide (ca. 20% in Ethanol) | TCI America |
| sodium tert-butoxide | TCI America |
| n-butyllithium (1.6M in hexanes) | Sigma-Aldrich |
| potassium carbonate | EMD Millipore |
| cesium carbonate | Alfa Aesar |
| potassium hydroxide | EMD Millipore |

-continued

| Compound | Supplier |
| --- | --- |
| triethylamine | Sigma-Aldrich |
| sodium bicarbonate | Sigma-Aldrich |
| ammonium chloride | VWR |
| Oxidants | |
| 1,3-Dibromo-5,5-dimethylhydantoin | Alfa Aesar |
| hydrogen peroxide, 30% | J.T. Baker |
| urea hydrogen peroxide adduct | Alfa Aesar |
| m-chloroperoxybenzoic acid | Alfa Aesar |
| Ligands | |
| 2-(Dicyclohexylphosphino)-2',4',6'-tri-i-propyl-1,1'-biphenyl (XPhos) | Strem |
| 2-(Di-t-butylphosphino)-3-methoxy-6-methyl-2'-4'-6'-tri-i-propyl-1,1'-biphenyl (RockPhos) | Strem |
| 2-(Di-t-butylphosphino)-3,6-dimethoxy-2',4',6'-tri-i-propyl-1,1'-biphenyl (t-buBrettPhos) | Strem |
| 1,1'bis(diphenylphospino)ferrocene | Strem |
| Catalysts | |
| tris(dibenzylideneacetone)dipalladium | Strem |
| palladium acetate | TCI America |
| allylpalladium(II) chloride dimer | Lancaster |
| copper acetate | Alfa Aesar |
| Methanesulfonato(2-(di-t-butylphosphino)-3,6-dimethoxy-2',4',6'-tri-i-propyl-1,1'-biphenyl)(2'-amino-1,1'-biphenyl-2-yl)palladium(II) (XPhos Precatalyst) | Strem |
| Methanesulfonato(2-(di-t-butylphosphino)-3-methoxy-6-methyl-2',4',6'-tri-i-propyl-1,1'-biphenyl)(2'-amino-1,1'-biphenyl-2-yl)palladium(II) (RockPhos Precatalyst) | Strem |
| Methanesulfonato(2-(di-t-butylphosphino)-3,6-dimethoxy-2',4',6'-tri-i-propyl-1,1'-biphenyl)(2'-amino-1,1'-biphenyl-2-yl)palladium(II) (t-BuBrettPhos Precatalyst) | Strem |
| Reagents | |
| p-tolylboronic acid | Aldrich Chemical |
| trimethylborate | Alfa Aesar |
| iodomethane | Alfa Aesar |
| triisopropylchlorosilane | Alfa Aesar |
| boron tribromide | Sigma-Aldrich |
| thionyl chloride | Alfa Aesar |
| trifluoromethanesulfonic anhydride | Oakwood |
| 2-(2H-Benzotriazol-2-yl)-4-(1,1,3,3-tetramethylbutyl)phenol | TCI America |
| m-cresol | Alfa Aesar |
| n-butanol | Sigma-Aldrich |
| methylamine hydrochloride | Aldrich Chemical |
| 4-n-hexylaniline | Alfa Aesar |
| hexylamine | Alfa Aesar |
| ammonia (0.5M in dioxane) | Sigma Alrich |
| scandium triflate | Strem |
| 4-methylbenzenethiol toluene | Alfa Aesar |
| potassium thioacetate | Alfa Aesar |
| 3,5-bis(trifluoromethyl)aniline | Alfa Aesar |
| 1-bromo-4-(heptadecafluorooctyl)benzene | Sigma Aldrich |
| 1-iodooctadecane | Alfa Aesar |

Structural Formulas of Compounds Disclosed

The table below presents a summary of the structural formulas for the compounds disclosed in this application and prepared in the syntheses presented below. This table is added merely for clarity and is not exhaustive.

| Structure | Example | MW | Name |
|---|---|---|---|
| benzotriazole-Ph(OH)(Br)-CH2C(CH3)2CH(CH3)2 derivative | 1 | 402.34 | 2-(2H-1,2,3-benzotriazol-2-yl)-6-bromo-4-(2,4,4-trimethylpentan-2-yl)phenol |
| benzotriazole-Ph(OMe)(Br)-CH2C(CH3)2CH(CH3)2 derivative | 1 | 416.36 | 2-(3-bromo-2-methoxy-5-(2,4,4-trimethylpentan-2-yl)phenyl)-2H-1,2,3-benzotriazole |
| benzotriazole-Ph(OCH2OCH3)(Br) derivative | 2 | | 2-(3-bromo-2-(methoxymethoxy)-5-(2,4,4-trimethylpentan-2-yl)phenyl)-2H-1,2,3-benzotriazole |
| benzotriazole-Ph(OMe)(Cl) derivative | 3 | | 2-(3-chloro-2-methoxy-5-(2,4,4-trimethylpentan-2-yl)phenyl)-2H-1,2,3-benzotriazole |
| benzotriazole-Ph(OMe)(OH) derivative | 4 | 353.47 | 3-(2H-1,2,3-benzotriazol-2-yl)-2-methoxy-5-(2,4,4-trimethylpentan-2-yl)phenol |
| benzotriazole-Ph(OMe)(O-n-Bu) derivative | 5 | 409.57 | 2-(3-butoxy-2-methoxy-5-(2,4,4-trimethylpentan-2-yl)phenyl)-2H-1,2,3-benzotriazole |

-continued

| Structure | Example | MW | Name |
|---|---|---|---|
| 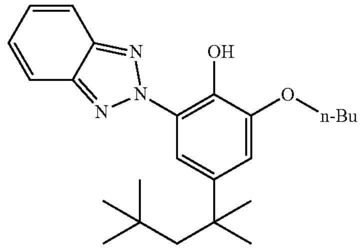 | 5 | 395.55 | 2-(2H-1,2,3-benzotriazol-2-yl)-6-butoxy-4-(2,4,4-trimethylpentan-2-yl)phenol |
| | 6 | 443.59 | 2-(2-methoxy-3-(m-tolyloxy)-5-(2,4,4-trimethylpentan-2-yl)phenyl)-2H-1,2,3-benzotriazole |
| | 6 | 429.56 | 2-(2H-1,2,3-benzotriazol-2-yl)-6-(m-tolyloxy)-4-(2,4,4-trimethylpentan-2-yl)phenol |
| | 7 | 443.59 | 2-(2-methoxy-3-(p-tolyloxy)-5-(2,4,4-trimethylpentan-2-yl)phenyl)-2H-1,2,3-benzotriazole |
| | 7 | 429.56 | 2-(2H-1,2,3-benzotriazole-2-yl)-6-(p-tolyloxy)-4-(2,4,4-trimethylpentan-2-yl)phenol |
| 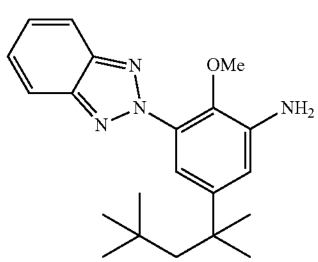 | 8 | 352.48 | 3-(2H-benzo[d][1,2,3]triazol-2-yl)-2-methoxy-5-(2,4,4-trimethylpentan-2-yl)aniline |

-continued

| Structure | Example | MW | Name |
|---|---|---|---|
| 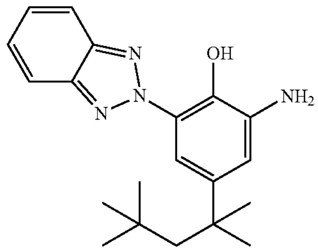 | 8 | 338.46 | 2-amino-6-(2H-benzo[d][1,2,3]triazol-2-yl)-4-(2,4,4-trimethylpentan-2-yl)phenol |
| | 9 | 366.51 | 3-(2H-1,2,3-benzotriazol-2-yl)-2-methoxy-N-methyl-5-(2,4,4-trimethylpentan-2-yl)aniline |
| | 9 | 352.48 | 2-(2H-1,2,3-benzotriazole-2-yl)-6-(methylamino)-4-(2,4,4-trimethylpentan-2-yl)phenol |
| | 10 | 351.47 | 3-(2H-benzo[d][1,2,3]triazol-2-yl)-N-hexyl-2-methoxy-5-(2,4,4-trimethylpentan-2-yl)aniline |
| | 10 | 422.62 | 2-(2H-benzo[d][1,2,3]triazol-2-yl)-6-(hexylamino)-4-(2,4,4-trimethylpentan-2-yl)phenol |
| 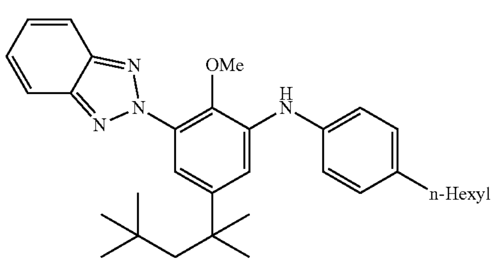 | 11 | 427.57 | 3-(2H-benzo[d][1,2,3]triazol-2-yl)-N-(4-hexylphenyl)-2-methoxy-5-(2,4,4-trimethylpentan-2-yl)aniline |

-continued

| Structure | Example | MW | Name |
|---|---|---|---|
| 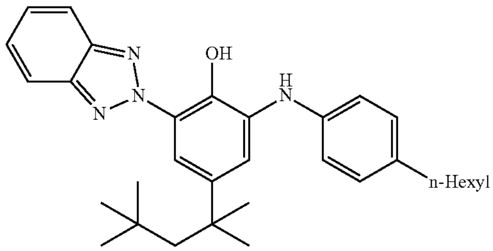 | 11 | 413.55 | 2-(2H-benzo[d][1,2,3]triazol-2-yl)-6-((4-hexylphenyl)amino)-4-(2,4,4-trimethylpentan-2-yl)phenol |
| | 12 | 558.68 | 2-(3-bromo-2-((triisopropylsilyl)oxy)-5-(2,4,4-trimethylpentan-2-yl)phenyl)-2H-benzo[d][1,2,3]triazole |
| | 12 | 495.78 | 2-(2H-1,2,3-benzotriazol-2-yl)-6-((triisopropylsilyl)oxy)-4-(2,4,4-trimethylpentan-2-yl)phenol |
| 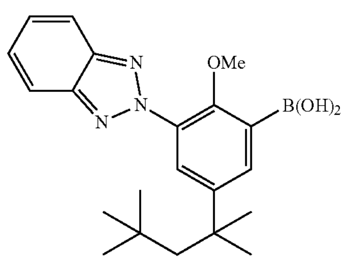 [SMILES: COc1c(B(O)O)cc(C(C)(C)CC(C)(C)C)cc1-n1nc2ccccc2n1] | 13 | 381.28 | (3-(2H-1,2,3-benzotriazol-2-yl)-2-methoxy-5-(2,4,4-trimethylpentan-2-yl)phenyl)boronic acid |
| | 14 | 687.93 | bis(3-(2H-1,2,3-benzotriazol-2-yl)-2-methoxy-5-(2,4,4-trimethylpentan-2-yl)phenyl)amine |
| | 14 | 659.88 | 6,6'-azanediylbis(2-(2H-benzo[d][1,2,3]triazol-2-yl)-4-(2,4,4-trimethylpentan-2-yl)phenol) |

-continued

| Structure | Example | MW | Name |
|---|---|---|---|
| | 15 | 701.96 | N-(3-(2H-benzo[d][1,2,3]triazol-2-yl)-2-methoxy-5-(2,4,4-trimethylpentan-2-yl)phenyl)-3-(2H-benzo[d][1,2,3]triazol-2-yl)-2-methoxy-N-methyl-5-(2,4,4-trimethylpentan-2-yl)aniline |
| | 15 | 673.91 | 6,6'-(methylazanediyl)bis(2-(2H-benzo[d][1,2,3]triazol-2-yl)-4-(2,4,4-trimethylpentan-2-yl)phenol |
| | 16 | 485.52 | 3-(2H-1,2,3-benzotriazol-2-yl)-2-methoxy-5-(2,4,4-trimethylpentan-2-yl)phenyl trifluoromethanesulfonate |
| | 16 | 688.92 | 2,2'-(oxybis(2-methoxy-5-(2,4,4-trimethylpentan-2-yl)-3,1-phenylene))bis(2H-benzo[d][1,2,3]triazole) |
| | 16 | 660.86 | 6,6'-oxybis(2-(2H-benzo[d][1,2,3]triazol-2-yl)-4-(2,4,4-trimethylpentan-2-yl)phenol |
| 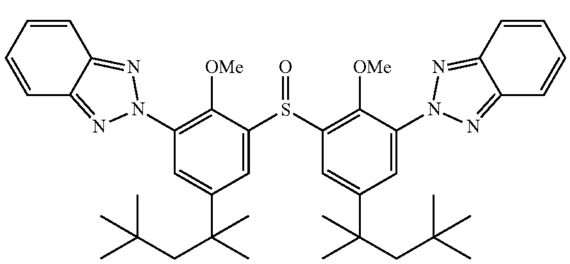 [SMILES: COc1c(-n2nc3ccccc3n2)cc(C(C)(C)CC(C)(C)C)cc1S(=O)c1cc(C(C)(C)CC(C)(C)C)cc(-n2nc3ccccc3n2)c1OC] | 17 | 720.98 | 2,2'-(sulfinylbis(2-methoxy-5-(2,4,4-trimethylpentan-2-yl)-3,1-phenylene))bis(2H-benzo[d][1,2,3]triazole) |

-continued

| Structure | Example | MW | Name |
|---|---|---|---|
| 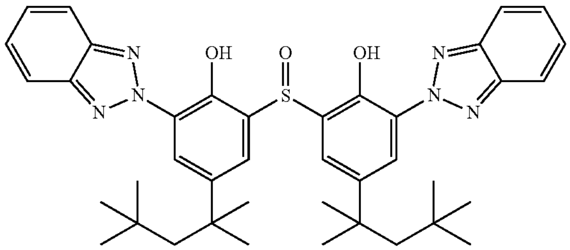 | 17 | 692.92 | 6,6'-sulfinylbis(2-(2H-benzo[d][1,2,3]triazol-2-yl)-4-(2,4,4-trimethylpentan-2-yl)phenol) |
| | 18 | 704.98 | bis(3-(2H-benzo[d][1,2,3]triazol-2-yl)-2-methoxy-5-(2,4,4-trimethylpentan-2-yl)phenyl)sulfane |
| | 18 | 676.92 | 6,6'-thiobis(2-(2H-benzo[d][1,2,3]triazol-2-yl)-4-(2,4,4-trimethylpentan-2-yl)phenol) |
| 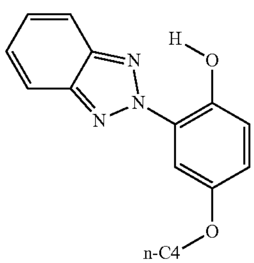 | 19 | 241.25 | 2-(2H-benzo[d][1,2,3]triazol-2-yl)-4-methoxyphenol |
| | 20 | 564.58 | 3-(2H-benzotriazol-2-yl)-N-(3,5-bis(trifluoromethyl)phenyl)-2-methoxy-5-(2,4,4-trimethylpentan-2-yl)aniline |
| | 20 | 550.55 | 2-(2H-benzotriazol-2-yl)-6-((3,5-bis(trifluoromethyl)phenyl)amino)-4-(2,4,4-trimethylpentan-2-yl)phenol |

-continued

| Structure | Example | MW | Name |
|---|---|---|---|
| | 21 | 846.63 | 3-(2H-benzotriazol-2-yl)-2-methoxy-N-(4-(perfluorooctyl)phenyl)-5-(2,4,4-trimethylpentan-2-yl)aniline |
| | 21 | 832.61 | 2-(2H-benzotriazol-2-yl)-6-((4-(perfluorooctyl)phenyl)amino)-4-(2,4,4-trimethylpentan-2-yl)phenol |
| | 22 | 459.65 | 2-(2-methoxy-3-(p-tolylthio)-5-(2,4,4-trimethylpentan-2-yl)phenyl)-2H-benzo[d][1,2,3]triazole |
| | 22 | 445.63 | 2-(2H-benzotriazol-2-yl)-6-(p-tolylthio)-4-(2,4,4-trimethylpentan-2-yl)phenol |
| 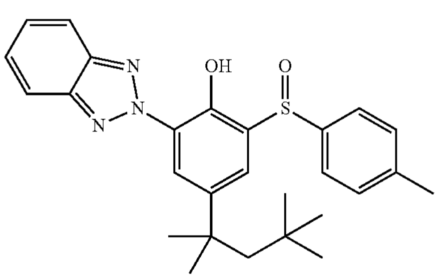 [SMILES: Cc1ccc(S(=O)c2cc(C(C)(C)CC(C)(C)C)cc(-n3nc4ccccc4n3)c2O)cc1] | 23 | 461.62 | 2-(2H-benzotriazol-2-yl)-6-(p-tolylsulfinyl)-4-(2,4,4-trimethylpentan-2-yl)phenol |

| Structure | Example | MW | Name |
|---|---|---|---|
| 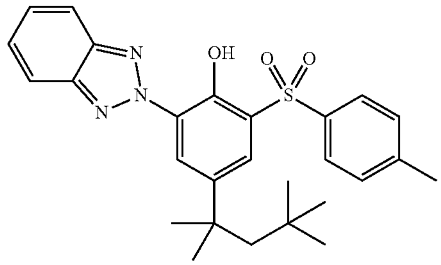 [SMILES: Cc1ccc(S(=O)(=O)c2cc(C(C)(C)CC(C)(C)C)cc(-n3nc4ccccc4n3)c2O)cc1] | 24 | 477.62 | 2-(2H-benzotriazol-2-yl)-6-tosyl-4-(2,4,4-trimethylpentan-2-yl)phenol |
| 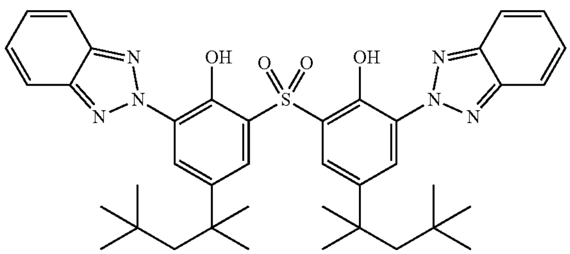 [SMILES: CC(C)(C)CC(C)(C)c1cc(-n2nc3ccccc3n2)c(O)c(S(=O)(=O)c2cc(C(C)(C)CC(C)(C)C)cc(-n3nc4ccccc4n3)c2O)c1] | 25 | 708.92 | 6,6'-sulfonylbis(2-(2H-benzotriazol-2-yl)-4-(2,4,4-trimethylpentan-2-yl)phenol) |
| 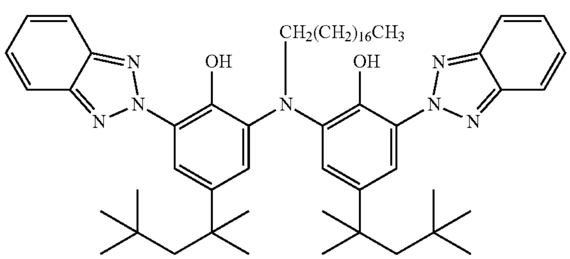 | 26 | 912.37 | 6,6'-(octadecylazanediyl)bis(2-(2H-benzotriazol-2-yl)-4-(2,4,4-trimethylpentan-2-yl)phenol) |

In the examples below automated flash chromatography (AFC) was carried out using an ISOLERA system available from Biotage, Inc, Charlottesville, Va., USA. For these purifications Biotage SNAP Ultra silica columns were used with a hexane/ethyl acetate gradient mixture.

All intermediates and products were confirmed using $^1$H and $^{13}$C Nuclear Magnetic Resonance (NMR) on a 500 MHz Bruker instrument. In some cases HRMS was also obtained.

A General Reaction Scheme I is presented below which was followed to prepare the compounds of this disclosure. Specific details are provided for each Example.

General Reaction Scheme I.

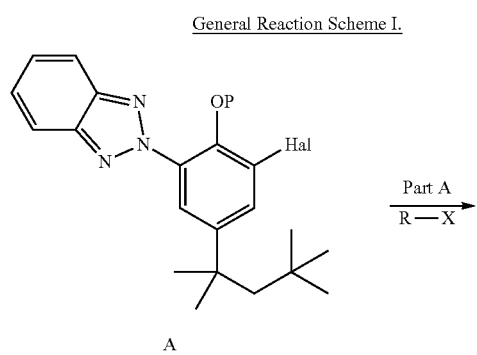

A

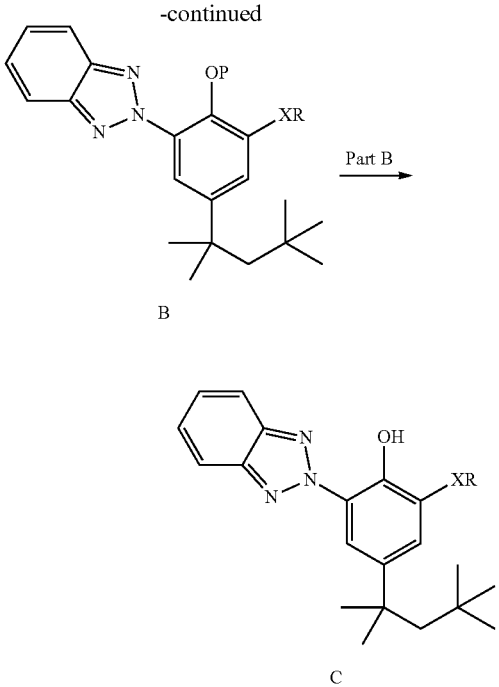

P = Protecting Group (alkyl, silyl)
Hal = Cl, Br, I
X = N, O, S
R = alkyl, aryl, H Part A: Cross-Coupling. Protected phenol A is subjected to cross-coupling conditions with either a palladium or copper catalyst. For specific reaction conditions, see each individual example.

Palladium Catalysis (Buchwald-Hartwig Cross-Coupling):

Buchwald, Hartwig, and coworkers have reported in the literature a transformation in which aryl halides can be converted to heteroatoms by use of a palladium catalyst and a bulky phosphine ligand. The following commercially available ligands (developed by Buchwald) have been used to synthesize benzotriazole phenolic analogs in which a heteroatom has been introduced in the ortho position (see compound B). These ligands can also be purchased already complexed to the palladium catalyst and are referred to as precatalysts.

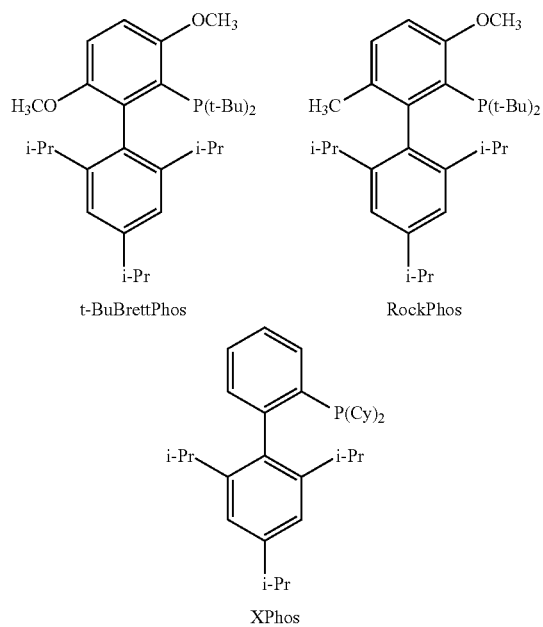

Copper Catalysis (Chan-Evans-Lam Coupling):

Copper can also be used to effect cross-coupling reactions between arylboronic acids and phenols, anilines, or arylthiols. This is considered to be a modification of the Ullmann condensation, as described in Kürti, L.; Czakó. *Strategic Applications of Named Reactions in Organic Synthesis,* 1$^{st}$ ed. Burlington: MA, 2005, pp. 464-465. The reaction is stoichiometric in copper salts and is typically performed under ambient conditions.

Part B: Deprotection of Methyl Ether. The methoxy ether benzotriazole (B, P=Me) was dissolved in dichloromethane (0.1 M) and cooled to −78° C. while stirring under $N_2$. Boron tribromide (1 equivalent per protected phenol) was added dropwise and the reaction mixture allowed to slowly warm to room temperature. When the reaction was complete (analysis by TLC), water was added dropwise and the mixture was stirred for 10 min. The organic layer was separated and the aqueous layer extracted with DCM (2×). The combined organic layers were washed with saturated aqueous $NaHCO_3$ and brine, dried ($Na_2SO_4$ or $MgSO_4$), filtered and concentrated. The residue was purified ($SiO_2$) to give products in 78-98% yield.

Example 1

Synthesis of 2-(3-bromo-2-methoxy-5-(2,4,4-trimethylpentan-2-yl)phenyl)-2H-1,2,3-benzotriazole (1)

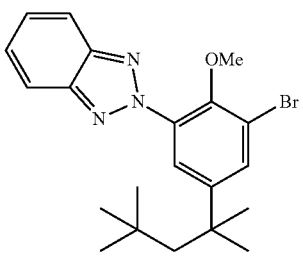 [SMILES: COc1c(Br)cc(C(C)(C)CC(C)(C)C)cc1-n1nc2ccccc2n1]

Part A: Bromination. 2-(2H-Benzotriazol-2-yl)-4-(1,1,3,3-tetramethylbutyl)phenol (100 g, 309 mmol) was placed in a 1 L round bottom flask fitted with a stir bar and dissolved in chloroform (500 mL). To this was added 1,3-dibromo-5,5-dimethylhydantoin (DBDMH) (45.95 g, 161 mmol) and the mixture stirred rt overnight. After such time, the mixture was filtered and concentrated to give a dark red residue. The residue was recrystallized from dichloromethane/ethanol to obtain white crystals. Multiple recrystallizations of the mother liquor yielded 113 g of pure product (91% yield).

Part B: Methylation. The reaction product from Part A was placed in a 1 L round bottom flask fitted with a stir bar and dissolved in acetonitrile (400 mL). Potassium carbonate (20.70 g, 150 mmol) was added followed by iodomethane (3.3 mL, 52.5 mmol). The mixture stirred rt overnight. After such time, the reaction mixture was partially concentrated, diluted with ethyl acetate and filtered over celite. The solution was concentrated, giving a thick beige oil, which eventually solidified over time to give 20.8 g (quantitative yield) of product.

Example 2

Synthesis of 2-(3-bromo-2-(methoxymethoxy)-5-(2,4,4-trimethylpentan-2-yl)phenyl)-2H-1,2,3-benzotriazole

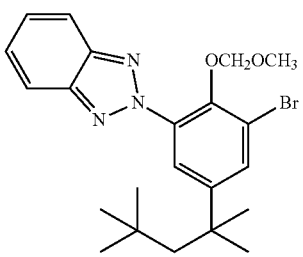

This procedure is similar to that described in *Organic Synthesis,* 2007, 84, 102. A 1 dram vial is fitted with a magnetic stirbar and charged with dimethoxymethane (0.33 mL, 3.72 mmol), toluene (1 mL) and $ZnBr_2$ (0.1 mg). Acetyl chloride (0.26 mL, 3.72 mmol) was added slowly, dropwise. After 2 h, the reaction mixture is cooled to 0° C. and diisopropylethylamine (0.54 mL, 3.1 mmol) is added to the reaction mixture slowly. The phenol is then added (1 g, 2.48 mmol) and the mixture stirred overnight. The solution is diluted with ethyl acetate (1 mL) and a saturated aqueous NH₄Cl solution (1 mL) is added and the mixture continued to stir for 10 min. The organic layer was separated and washed with brine, dried, filtered and purified by flash column chromatography to give a beige solid (0.99 g, 89% yield) after evaporation.

Example 3

Synthesis of 2-(3-chloro-2-methoxy-5-(2,4,4-trimethylpentan-2-yl)phenyl)-2H-1,2,3-benzotriazole

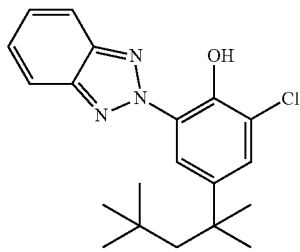 [SMILES: CC(C)(C)CC(C)(C)c1cc(Cl)c(O)c(-n2nc3ccccc3n2)c1]

Part A: Chlorination. 2-(2H-Benzotriazol-2-yl)-4-(1,1,3,3-tetramethylbutyl)phenol (2 g, 6.18 mmol) was placed in a 200 mL round bottom flask fitted with a stir bar and dissolved in acetonitrile (65 mL). To this was added N-chlorosuccinimide (NCS) (0.908 g, 6.802 mmol) and the mixture refluxed overnight. After such time, the mixture was cooled to rt and quenched with 10% aqueous Na₂S₂O₃ and extracted with EtOAc. The combined organic layers were dried (Na₂SO₄), filtered, and concentrated to give a beige solid in quantitative yield. No further purification was performed.

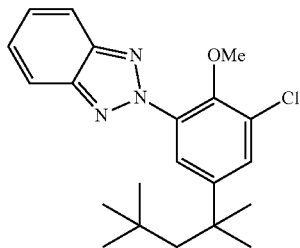 [SMILES: COc1c(Cl)cc(C(C)(C)CC(C)(C)C)cc1-n1nc2ccccc2n1]

Part B: Methylation. The reaction product from Part A (1.5 g, 4.19 mmol) was placed in a 100 mL round bottom flask fitted with a stir bar and dissolved in acetonitrile (50 mL). Potassium carbonate (1.738 g, 12.57 mmol) was added followed by iodomethane (0.27 mL, 4.40 mmol). The mixture stirred rt overnight. After such time, the reaction mixture was partially concentrated, diluted with ethyl acetate and filtered over celite, concentrated, and purified by AFC. A beige oil was isolated, which eventually solidified over time to give 0.96 g (62%) of product.

Example 4

3-(2H-1,2,3-benzotriazol-2-yl)-2-methoxy-5-(2,4,4-trimethylpentan-2-yl)phenol

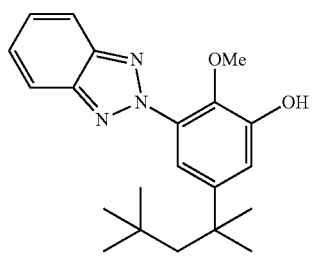 [SMILES: COc1c(O)cc(C(C)(C)CC(C)(C)C)cc1-n1nc2ccccc2n1]

Into a vial equipped with a stir bar was placed benzotriazole 1 prepared in Example 1 (5.10 g, 12.24 mmol), potassium hydroxide (2.06 g, 36.72 mmol), t-BuBrettPhos ligand (30 mg, 0.06 mmol), and t-BuBrettPhos Pd precatalyst (40.6 mg, 0.06 mmol). The vial was fitted with a septa cap and evacuated and backfilled with N₂. 1,4-Dioxane (24 mL) and deionized water (4.4 mL) were added and the reaction mixture stirred overnight at 100° C. After such time, the reaction was diluted with EtOAc and acidified with 10% aq HCl and stirred for an additional 10 min. After such time, the organic layer was separated and the aqueous layer extracted with EtOAc (2x). The combined organic layers were washed with saturated aqueous NaHCO₃, brine, dried (Na₂SO₄), filtered and concentrated to give a residue that was purified via flash column chromatography. A beige glassy solid was isolated (3.57 g, 83% yield).

Example 5

2-(2H-1,2,3-benzotriazol-2-yl)-6-butoxy-4-(2,4,4-trimethylpentan-2-yl)phenol

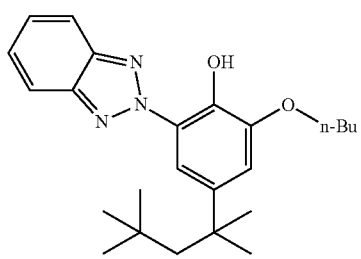

Into three flame dried 40-dram vials, each equipped with a stir bar and activated 4 Å mol sieves was placed benzotriazole 1 prepared in Example 1, (4.179 g, 10.04 mmol), cesium carbonate (4.91 g, 15.06 mmol), allylpalladium chloride dimer (18.4 mg, 0.5 mol %), and RockPhos ligand (23.4 mg, 0.5 mol %). Each vial was fitted with a septa cap and evacuated and backfilled with N₂ (3x). Toluene (10 mL), followed by anhydrous n-butanol (1.8 mL, 20.08 mmol) was added to each vial. The vials were placed on a ChemGlass reaction block and heated to 100° C. for 72 h. After such time, the reaction mixtures were combined, filtered over celite, and concentrated. The crude residue was purified via flash column chromatography to give a pale yellow solid (9.80 g, 79% yield). Following Part B (General Reaction Scheme I), the free phenol was isolated as a beige solid after purification by flash column chromatography (8.50 g, 85% yield).

Example 6

2-(2H-1,2,3-benzotriazol-2-yl)-6-(m-tolyloxy)-4-(2,4,4-trimethylpentan-2-yl)phenol

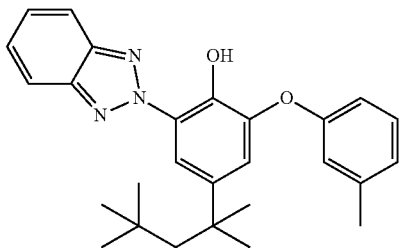 [SMILES: Cc1cccc(Oc2cc(C(C)(C)CC(C)(C)C)cc(-n3nc4ccccc4n3)c2O)c1]

Into two flame dried 40-dram vials, each equipped with a stir bar and activated 4 Å mol sieves was placed benzotriazole 1 prepared in Example 1, (4.16 g, 10 mmol), potassium phosphate (4.25 g, 20 mmol), palladium(II) acetate (45 mg, 2 mol %), and RockPhos ligand (93 mg, 2 mol %). Each vial was fitted with a septa cap and evacuated and backfilled with $N_2$ (3×). Toluene (10 mL), followed by m-cresol (1.3 mL, 12 mmol) was added to each vial. The vials were placed on a ChemGlass reaction block and heated to 100° C. for 16 h. After such time, the reaction mixtures were combined, filtered over celite, and concentrated. The crude residue was purified via flash column chromatography to give a beige solid (7.07 g, 80% yield. Following Part B (General Reaction Scheme I), the free phenol was isolated as a beige solid after purification by flash column chromatography (6.50 g, 98% yield).

Example 7

2-(2H-1,2,3-benzotriazol-2-yl)-6-(p-tolyloxy)-4-(2,4,4-trimethylpentan-2-yl)phenol

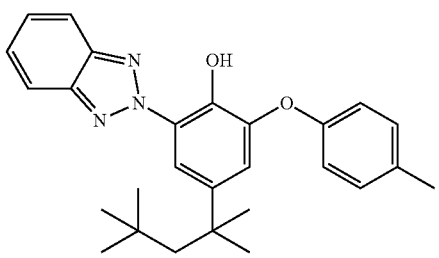 [SMILES: Cc1ccc(Oc2cc(C(C)(C)CC(C)(C)C)cc(-n3nc4ccccc4n3)c2O)cc1]

Into a vial equipped with a stir bar was placed the reaction product from Example 4 (61 mg, 0.1726 mmol), p-tolylboronic acid (23.5 mg, 0.1726 mmol), copper(II) acetate (31.3 mg, 0.1726 mmol), triethylamine (0.072 mL, 0.5177 mmol), and dichloromethane (1.7 mL). The vial was placed under a gentle stream of air and stirred rt overnight. After such time, the mixture was diluted with dichloromethane, filtered over celite, concentrated and purified to give a yellow foam (53.4 mg, 70% yield). Following Part B (General Reaction Scheme I), the free phenol was isolated as a beige solid (48 mg, 99% yield).

Example 8

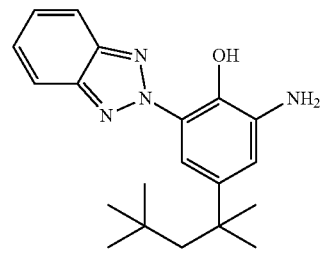 [SMILES: CC(C)(C)CC(C)(C)c1cc(N)c(O)c(-n2nc3ccccc3n2)c1]

Part A. To an oven-dried Schlenk flask fitted with a stir bar was added 4 Å molecular sieves, sodium tert-butoxide (23.37 mmol, 2.25 g), $Pd_2(dba)_3$ (0.33 mmol, 306 mg), XPhos (0.83 mmol, 398 mg) and benzotriazole 1 prepared in Example 1, (16.69 mmol, 6.95 g). The flask was then evacuated and flushed with $N_2$ (3×) and ammonia in dioxane (0.5 M, 100 mL) was added via cannula. The Schlenk flask was closed and heated to 130° C. for 16 h. After such time, the reaction mixture was diluted with EtOAc, filtered, and concentrated. The crude oil was purified via flash column chromatography to give a beige solid which was carried on to Part B (General Reaction Scheme I). Besides the dimer described in Example 14 below, a second compound was also isolated, which was identified as the mono-aniline (0.79 g, 13% yield). This compound was subjected to the standard deprotection conditions (Part B, General Reaction Scheme I), and the free phenol was isolated as a yellow solid (0.67 g, 85% yield).

Example 9

2-(2H-1,2,3-benzotriazol-2-yl)-6-(methylamino)-4-(2,4,4-trimethylpentan-2-yl)phenol

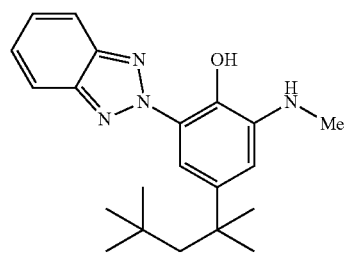 [SMILES: CNc1cc(C(C)(C)CC(C)(C)C)cc(-n2nc3ccccc3n2)c1O]

Into a flame dried vial equipped with a stir bar was placed benzotriazole 1 prepared in Example 1, (416 mg, 1 mmol), tris(dibenzylideneacetone)dipalladium(0) (20 mg, 0.01 mmol), XPhos ligand (20 mg, 0.04 mmol), sodium tert-butoxide (288 mg, 3 mmol), and methylamine hydrochloride (203 mg, 3 mmol). The vial was fitted with a septa cap and evacuated and backfilled with $N_2$. Dioxane (5 mL) was added and the reaction was heated to 130° C. for 16 h. After such time, the mixture was cooled to rt, diluted with EtOAc and filtered over celite. The residue was purified via AFC. A white solid was isolated (325 mg, 89% yield). Following Part B (General Reaction Scheme I), gave the free phenol as a yellow solid (180 mg, 78% yield).

Example 10

2-(2H-benzo[d][1,2,3]triazol-2-yl)-6-(hexylamino)-4-(2,4,4-trimethylpentan-2-yl)phenol

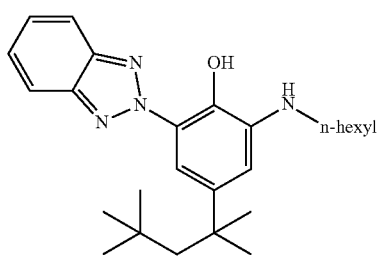

Into three flame dried vials equipped with a stir bar was placed benzotriazole 1 prepared in Example 1, (1.66 g, 4 mmol), tris(dibenzylideneacetone)dipalladium(0) (73.3 mg, 0.08 mmol), XPhos ligand (95.3 mg, 0.2 mmol), sodium tert-butoxide (538 mg, 5.6 mmol), and 1-hexylamine (0.74 mL, 5.6 mmol). The vial was fitted with a septa cap and evacuated and backfilled with $N_2$. Dioxane (20 mL) was added and the reaction was heated to 130° C. for 16 h. After such time, the mixtures were cooled to rt, combined, diluted with EtOAc and filtered over celite. The residue was purified via AFC. A beige solid was isolated (3.88 g, 74% yield). Following Part B (General Reaction Scheme I), gave the free phenol as a yellow solid (3.32, 88% yield).

Example 11

2-(2H-benzo[d][1,2,3]triazol-2-yl)-6-((4-hexylphenyl)amino)-4-(2,4,4-trimethylpentan-2-yl)phenol

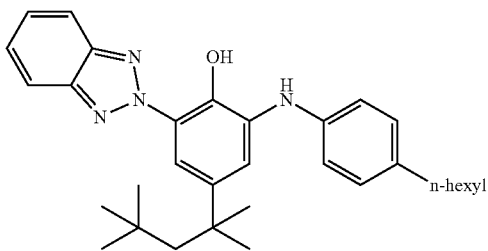

Into three flame dried vials equipped with a stir bar was placed benzotriazole 1 prepared in Example 1, (1.66 g, 4 mmol), tris(dibenzylideneacetone)dipalladium(0) (73.3 mg, 0.08 mmol), XPhos ligand (95.3 mg, 0.2 mmol), sodium tert-butoxide (538 mg, 5.6 mmol), and 4-hexylaniline (1 mL, 5.6 mmol). The vial was fitted with a septa cap and evacuated and backfilled with $N_2$. Dioxane (20 mL) was added and the reaction was heated to 130° C. for 16 h. After such time, the mixtures were cooled to rt, combined, diluted with EtOAc and filtered over celite. The residue was purified via AFC. A beige solid was isolated (3.88 g, 74% yield). Following Part B (General Reaction Scheme I), gave the free phenol as a yellow solid (4.67 g, 96% yield).

Example 12

2-(2H-1,2,3-benzotriazol-2-yl)-6-((triisopropylsilyl)oxy)-4-(2,4,4-trimethylpentan-2-yl)phenol

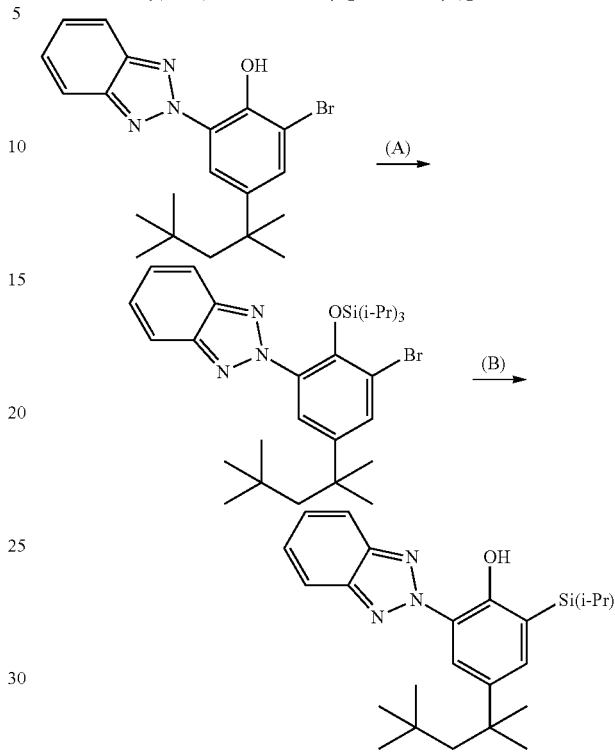

Part A. The reaction product from Example 1 was silylated with triisopropylchlorosilane (TIPS-Cl) following standard procedures.

Part B. The reaction product from Part A (1.57 g, 2.81 mmol) was placed into a round bottom flask containing a stir bar and charged with $N_2$. THF (20 mL) was added and the flask cooled to −78° C. n-Butyl lithium (1.8 mL, 2.81 mmol) was added and the mixture was allowed to slowly warm to rt and stir for 3 h. After such time, the reaction was quenched with saturated ammonium chloride and the product extracted with EtOAc (3×). The combined organic layers were washed with brine, dried and filtered. The crude residue was purified by AFC to give a colorless solid (0.74 g, 55% yield).

Example 13

Synthesis of (3-(2H-1,2,3-benzotriazol-2-yl)-2-methoxy-5-(2,4,4-trimethylpentan-2-yl)phenyl)boronic acid

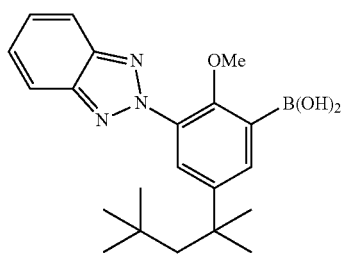 [SMILES: COc1c(B(O)O)cc(C(C)(C)CC(C)(C)C)cc1-n1nc2ccccc2n1]

Into a flame dried round bottom flask equipped with a stir bar was placed benzotriazole 1 prepared in Example 1, (1.936 mmol, 0.806 g) and cooled to −78° C. under $N_2$.

n-Butyl lithium (1.6M, 1.33 mL) was added slowly. After 10 min, trimethylborate (0.28 mL, 2.517 mmol) was added dropwise. The mixture stirred for 1.5 h at −78° C., then 1 h at 0° C. After such time, the mixture was quenched with 10% aq HCl (1 mL) and continued to stir for 10 min before being diluted with ethyl acetate. The organic layer was separated and the aqueous layer extracted (2×). The combined organic layers were washed with brine, dried and filtered. The crude residue was purified via flash column chromatography, giving an ivory colored solid (0.451 g. 61% yield).

Example 14

6,6'-azanediylbis(2-(2H-benzo[d][1,2,3]triazol-2-yl)-4-(2,4,4-trimethylpentan-2-yl)phenol)

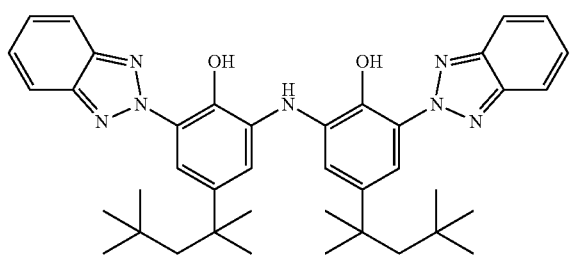 [SMILES: CC(C)(C)CC(C)(C)c1cc(Nc2cc(C(C)(C)CC(C)(C)C)cc(-n3nc4ccccc4n3)c2O)c(O)c(-n2nc3ccccc3n2)c1]

Part A. To an oven-dried Schlenk flask fitted with a stir bar was added 4 Å molecular sieves, sodium tert-butoxide (23.37 mmol, 2.25 g), Pd$_2$(dba)$_3$ (0.33 mmol, 306 mg), XPhos (0.83 mmol, 398 mg) and benzotriazole 1 prepared in Example 1, (16.69 mmol, 6.95 g). The flask was then evacuated and flushed with N$_2$ (3×) and ammonia in dioxane (0.5 M, 100 mL) was added via cannula. The Schlenk flask was closed and heated to 130° C. for 16 h. After such time, the reaction mixture was diluted with EtOAc, filtered, and concentrated. The crude oil was purified via flash column chromatography to give a beige solid.

Part B. The product of Part A was dissolved in dichloromethane (150 mL) and cooled to −78° C. while stirring under N$_2$. Boron tribromide (17.10 mmol, 1.6 mL) was added dropwise and the reaction mixture allowed to slowly warm to rt. When the reaction was complete (analysis by TLC), water was added dropwise and the mixture was stirred for 10 min. The organic layer was separated and the aqueous layer extracted with DCM (2×). The combined organic layers were washed with saturated aqueous NaHCO$_3$ and brine, dried (Na$_2$SO$_4$ or MgSO$_4$), filtered and concentrated. The residue was recrystallized from hot acetone to give a yellow crystalline solid (3.38 g, 61% yield from 1).

Example 15

6,6'-(methylazanediyl)bis(2-(2H-benzo[d][1,2,3]triazol-2-yl)-4-(2,4,4-trimethylpentan-2-yl)phenol)

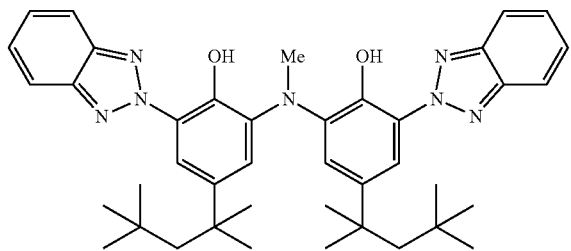

Part A. The reaction product from Example 14, Part A (12.79 mmol, 8.8 g) was dissolved in dimethylformamide (120 mL) and to this, sodium hydride (14.07 mmol, 0.56 g) was added under a stream of N$_2$ at rt. The mixture was stirred 10 min and then iodomethane (14.07 mmol, 0.88 mL) was added and stirring continued for another 2 h. The reaction was quenched with saturated aq ammonium chloride and extracted with EtOAc (3×). The combined organic layers were washed with water and then brine, dried with Na$_2$SO$_4$, filtered and concentrated. No further purification was performed.

Part B. The product of Part B was dissolved in dichloromethane (150 mL) and cooled to −78° C. while stirring under N$_2$. Boron tribromide (17.10 mmol, 1.6 mL) was added dropwise and the reaction mixture allowed to slowly warm to rt. When the reaction was complete (analysis by TLC), water was added dropwise and the mixture was stirred for 10 min. The organic layer was separated and the aqueous layer extracted with DCM (2×). The combined organic layers were washed with saturated aqueous NaHCO$_3$ and brine, dried (Na$_2$SO$_4$ or MgSO$_4$), filtered and concentrated. The residue was recrystallized from hot acetone to give a yellow crystalline solid (6.74 g, 60% yield from 1).

Example 16

6,6'-oxybis(2-(2H-benzo[d][1,2,3]triazol-2-yl)-4-(2,4,4-trimethylpentan-2-yl)phenol)

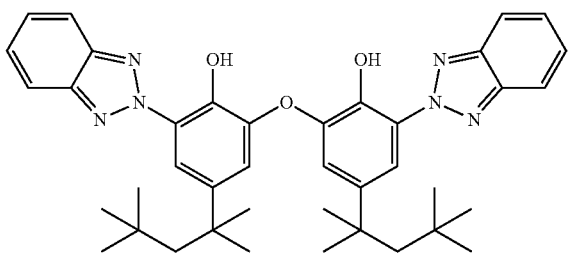 [SMILES: CC(C)(C)CC(C)(C)c1cc(Oc2cc(C(C)(C)CC(C)(C)C)cc(-n3nc4ccccc4n3)c2O)c(O)c(-n2nc3ccccc3n2)c1]

Part A. The reaction product from Example 4 was triflated using standard procedures. To form the compound 3-(2H-1,2,3-benzotriazol-2-yl)-2-methoxy-5-(2,4,4-trimethylpentan-2-yl)phenyl trifluoromethanesulfonate:

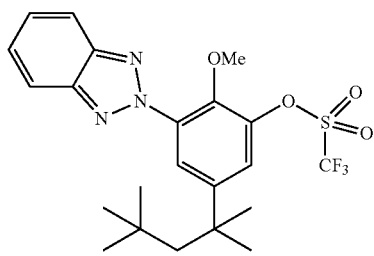 [SMILES: COc1c(OS(=O)(=O)C(F)(F)F)cc(C(C)(C)CC(C)(C)C)cc1-n1nc2ccccc2n1]

Part B. The reaction product (0.99 mmol, 482 mg) from Part A was then placed into a flame-dried vial along with the reaction product from Example 4 (0.99 mmol, 351 mg), potassium phosphate (1.99 mmol, 421 mg) and molecular sieves. The vial was then evacuated and flushed with N$_2$ (3×) and toluene (10 mL) was added. The reaction mixture was stirred for 72 h at 130° C. After such time, the mixture was cooled, filtered, and purified by flash column chromatography to obtain 5 as a white solid (73 mg, 11% yield). Following the procedure from Example 14, Part B, the product was obtained as an amber-colored crystalline solid (0.052 g, 76% yield).

Example 17

6,6'-sulfinylbis(2-(2H-benzo[d][1,2,3]triazol-2-yl)-4-(2,4,4-trimethylpentan-2-yl)phenol)

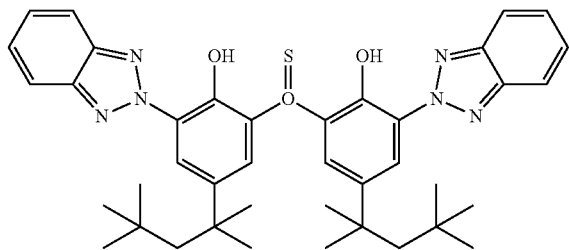

6,6'-Thiobis(2-(2H-benzotriazol-2-yl)-4-(2,4,4-trimethylpentan-2-yl)phenol) from Example 18 was oxidized using a literature procedure (Org Lett, 1999, 1, 189). 6,6'-Thiobis (2-(2H-benzotriazol-2-yl)-4-(2,4,4-trimethylpentan-2-yl) phenol) (7.39 mmol, 5.0 g) was dissolved in ethanol (5 mL) along with scandium triflate (0.74 mmol, 364 mg) and hydrogen peroxide.urea adduct (8.5 mmol, 820 mg). The reaction stirred at 80° C. overnight and the white precipitate was filtered and washed with water and ethanol. A 2:1 mixture of the sulfoxide:sulfone was isolated (4.18 g, 81% yield).

An alternative procedure can also be used. Benzotriazole 1 prepared in Example 1, (12 mmol, 5.0 g) was dissolved in THF under N$_2$ and cooled to −78° C. n-Butyl lithium (1.6M, 7.9 mL) was added slowly and the reaction stirred for 30 min. After such time, thionyl chloride (5.88 mmol, 0.43 mL) was added and the reaction allowed to slowly warm to rt. After 2 h, the reaction was quenched with saturated ammonium chloride and the product was extracted with ethyl acetate (3×). The combined organic layers were washed with brine, dried (Na$_2$SO$_4$), and filtered. The crude product was purified by flash column chromatography to give a white solid (1.2 g, 28% yield). Following the procedure from Example 14, Part B, the product was obtained as an amber-colored crystalline solid (0.73 g, 63% yield).

Example 18

6,6'-thiobis(2-(2H-benzo[d][1,2,3]triazol-2-yl)-4-(2,4,4-trimethylpentan-2-yl)phenol)

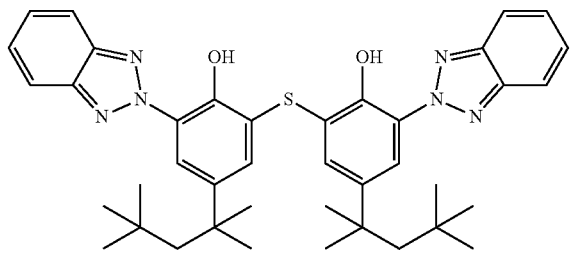

To a flame dried vial equipped with a stir bar was placed 3-bromo-2-methoxy-5-(2,4,4-trimethylpentan-2-yl)phenyl)-2H-1,2,3-benzotriazole (0.416 g, 1 mmol), potassium thioacetate (0.057 g, 0.5 mmol), Tris(dibenzylideneacetone)dipalladium(0) (0.023 g, 0.025 mmol), 1,1'-Bis(diphenylphosphino)ferrocene (0.028 g, 0.05 mmol) and potassium phosphate (0.127 g, 0.6 mmol). The vial was then evacuated and flushed with N$_2$ (3×) and toluene (0.5 mL) and acetone (0.25 mL) was added. The reaction mixture was stirred for 72 h at 130° C. After such time, the mixture was cooled, filtered, and purified by flash column chromatography to obtain 5 as a white solid (0.240 g, 68% yield). Following the procedure from Example 10, Part B, the product was obtained as a white solid (0.230 g, 99% yield).

A specialized reaction different from the above General Reaction Scheme I was used to prepare Phenol-19 as shown in Example 19 below.

Example 19

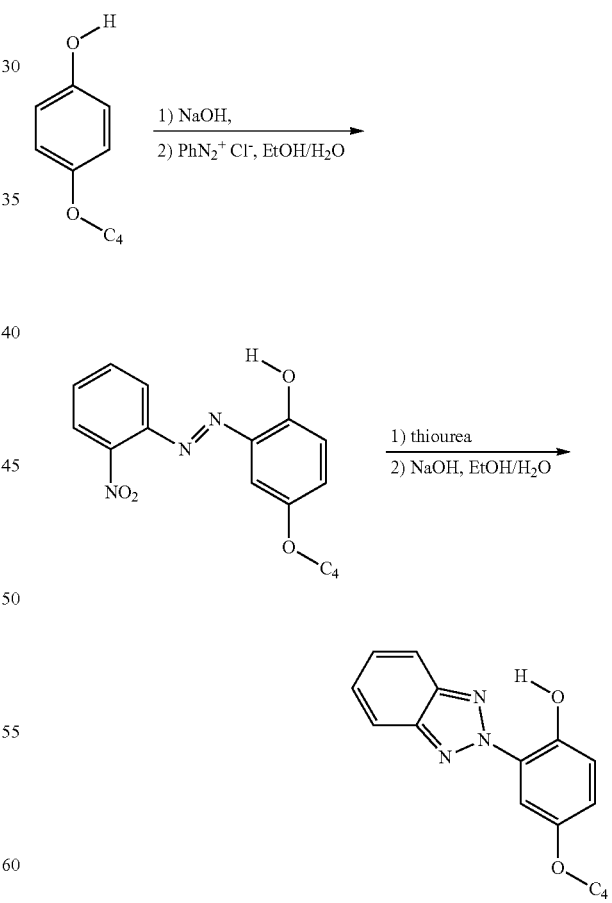

The diazo compound above as synthesized following standard diazotization procedure (WO008131921; Bioorg. Med. Chem. Lett. 2010, 20, 4193-4195), followed by reductive cyclization to give Phenol-19.

Example 20

2-(2H-benzotriazol-2-yl)-6-((3,5-bis(trifluoromethyl)phenyl)amino)-4-(2,4,4-trimethylpentan-2-yl)phenol

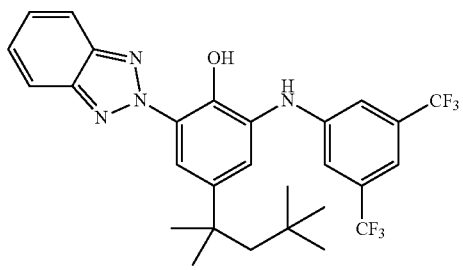 [SMILES: CC(C)(C)CC(C)(C)c1cc(Nc2cc(C(F)(F)F)cc(C(F)(F)F)c2)c(O)c(-n2nc3ccccc3n2)c1]

Into a 250 mL Schlenk flask equipped with a stir bar was placed benzotriazole 1 prepared in Example 1, (20.0 g, 48.03 mmol), tris(dibenzylideneacetone)dipalladium(0) (1.04 g, 1.14 mmol), XPhos ligand (1.35 g, 2.75 mmol), sodium tert-butoxide (7.63 g, 79.4 mmol), and 3,5-bis(trifluoromethyl)aniline (8 mL, 51.36 mmol). The Schlenk flask evacuated and backfilled with $N_2$. Dioxane (200 mL) was added and the reaction was heated to 130° C. for 16 h. After such time, the mixture was cooled to rt, diluted with EtOAc, filtered over celite and concentrated. The residue was purified via AFC. A brown solid was isolated (26.8 g, 98% yield). Following Part B (General Reaction Scheme I), gave the free phenol as a yellow solid (21.3 g, 82% yield).

Example 21

2-(2H-triazol-2-yl)-6-((4-(perfluorooctyl)phenyl)amino)-4-(2,4,4-trimethylpentan-2-yl)phenol

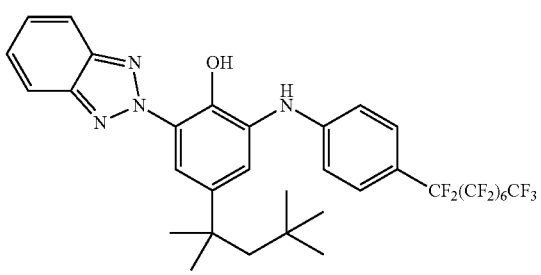

Into two flame dried 40-dram vials, each equipped with a stir bar was placed the product from Example 8, Part A (1.162 g, 3.30 mmol), 1-bromo-4-(heptadecafluorooctyl)benzene (2.0 g, 3.30 mmol), tris(dibenzylideneacetone)dipalladium(0) (60.4 mg, 0.066 mmol), XPhos ligand (80 mg, 0.163 mmol), and sodium tert-butoxide (444 mg, 4.62 mmol). Each vial was fitted with a septa cap and evacuated and backfilled with $N_2$. Dioxane (20 mL) was added to each vial and the vials were placed on a ChemGlass reaction block and heated to 130° C. for 16 h. After such time, the mixtures were cooled to rt, diluted with EtOAc, combined, and filtered over celite and concentrated. The residue was purified via AFC. A brown solid was isolated (4.41 g, 79% yield). Following Part B (General Reaction Scheme I), gave the free phenol as a yellow solid (3.41 g, 79% yield).

Example 22

2-(2H-benzotriazol-2-yl)-6-(p-tolylthio)-4-(2,4,4-trimethylpentan-2-yl)phenol benzotriazole

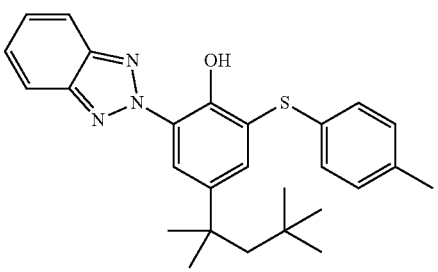 [SMILES: Cc1ccc(Sc2cc(C(C)(C)CC(C)(C)C)cc(-n3nc4ccccc4n3)c2O)cc1]

Into a flame dried vial equipped with a stir bar was placed 2-(2H-benzo[1,2,3]triazol-2-yl)-6-bromo-4-(2,4-dimethylpentan-2-yl)phenol (2.88 g, 6.92 mmol), tris(dibenzylideneacetone)dipalladium(0) (0.317 g, 0.346 mmol), 1,1'bis(diphenylphospino)ferrocene (0.383 g, 0.692 mmol), potassium phosphate (1.76 g, 8.30 mmol), and 4-methylbenzenethiol toluene (1.031 g, 8.30 mmol). The vial was fitted with a septa cap and evacuated and backfilled with $N_2$. Toluene (14 mL) was added and the reaction was heated to 110° C. for 16 h. After such time, the mixtures were cooled to rt, combined, diluted with EtOAc and filtered over celite. The residue was purified via AFC. A beige solid was isolated (3.09 g, 97% yield). Following Part B (General Reaction Scheme I), gave the free phenol as an ivory-colored solid (2.70 g, 90% yield).

Example 23

2-(2H-benzotriazol-2-yl)-6-(p-tolylsulfinyl)-4-(2,4,4-trimethylpentan-2-yl)phenol

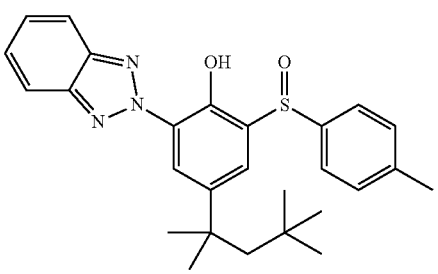 [SMILES: Cc1ccc(S(=O)c2cc(C(C)(C)CC(C)(C)C)cc(-n3nc4ccccc4n3)c2O)cc1]

The following was adapted from a literature procedure (Org Lett. 2003, 5, 235). Aryl sulfide from Example 22 (1.2 g, 2.69 mmol) was added to a vial equipped with a stir bar. Ethanol (7 mL) and hydrogen peroxide (30%, 1.5 mL) were added and $N_2$ was bubbled through the mixture for several minutes. Scandium triflate (0.265 g, 0.539 mmol) was added and the mixture allowed to stir rt overnight. After such time, the reaction was quenched with $H_2O$ (2 mL) and filtered. The filtrate was purified by AFC and a white solid was obtained (0.764 g, 61% yield). Another 0.167 g of recrystallized product from the mother liquor was obtained for a total of 0.931 g (75% yield) of product.

Example 24

2-(2H-benzotriazol-2-yl)-6-tosyl-4-(2,4,4-trimethyl-pentan-2-yl)phenol

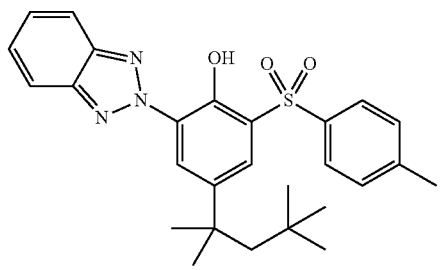 [SMILES: Cc1ccc(S(=O)(=O)c2cc(C(C)(C)CC(C)(C)C)cc(-n3nc4ccccc4n3)c2O)cc1]

Aryl sulfide from Example 22 (1.5 g, 3.366 mmol) was dissolved in dichloromethane (17 mL) in a vial equipped with a stir bar. m-Chloroperoxybenzoic acid, 50 wt % (2.56 g, 7.40 mmol) was added and the reaction stirred until complete by TLC. The reaction was then quenched with saturated aqueous NaHCO$_3$ and the organic layer separated, dried (Na$_2$SO$_4$), filtered, and concentrated. It was purified by washing with EtOAc and filtering. A white solid was obtained (1.34 g, 83% yield).

Example 25

6,6'-sulfonylbis(2-(2H-benzotriazol-2-yl)-4-(2,4,4-trimethylpentan-2-yl)phenol)

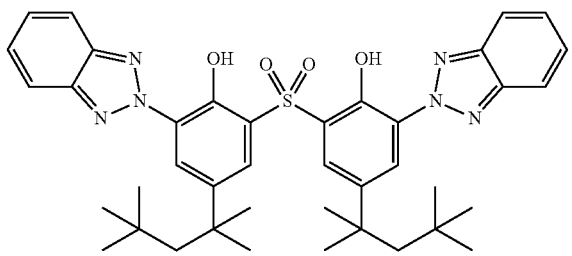

6,6'-Sulfonylbis(2-(2H-benzotriazol-2-yl)-4-(2,4,4-trimethylpentan-2-yl)phenol) was synthesized in a similar fashion as Example 24. Aryl sulfide from Example 18 (4.5 g, 6.6 mmol) was dissolved in dichloromethane (33 mL) in a flask equipped with a stir bar. m-Chloroperoxybenzoic acid, 50 wt % (7.40 mmol, 5.05 g) was added and the reaction stirred until complete by TLC. The reaction was then quenched with sat'd aqueous NaHCO$_3$ and the organic layer separated, dried (Na$_2$SO$_4$), filtered, and concentrated. It was purified by washing with EtOAc and filtering. A white solid was obtained (2.9 g, 62% yield).

Example 26

6,6'-(octadecylazanediyl)bis(2-(2H-benzotriazol-2-yl)-4-(2,4,4-trimethylpentan-2-yl)phenol)

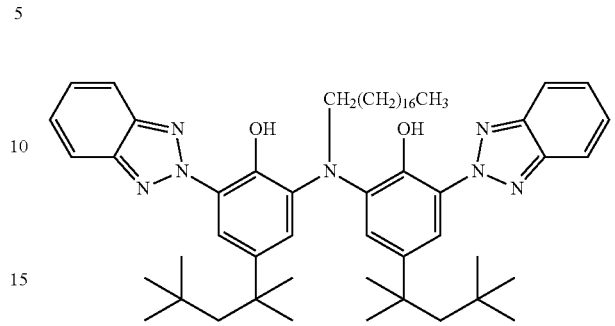

Part A. The reaction product from Example 14, Part A (4.0 g, 5.81 mmol) was dissolved in dimethylformamide (60 mL) and to this, sodium hydride (6.40 mmol, 256 mg) was added under a stream of N$_2$ at rt. The mixture was stirred 10 min and then 1-iodooctadecane (6.40 mmol, 2.43 g) was added and stirring continued for another 2 h. The reaction was quenched with saturated aq ammonium chloride and extracted with EtOAc (3×). The combined organic layers were washed with water and then brine, dried with Na$_2$SO$_4$, filtered and concentrated. No further purification was performed.

Part B. The product of Part A was dissolved in dichloromethane (40 mL) and cooled to temperature of −78° C. while stirring under N$_2$. Boron tribromide (12.20 mmol, 1.2 mL) was added dropwise and the reaction mixture allowed to slowly warm to rt. When the reaction was complete (analysis by TLC), water was added dropwise and the mixture was stirred for 10 min. The organic layer was separated and the aqueous layer extracted with DCM (2×). The combined organic layers were washed with saturated aqueous NaHCO$_3$ and brine, dried (Na$_2$SO$_4$ or MgSO$_4$), filtered and concentrated to give a viscous oil (5.16 g, 97% yield).

What is claimed is:

1. A composition comprising a substituted benzotriazole phenol with the structure of Formula I:

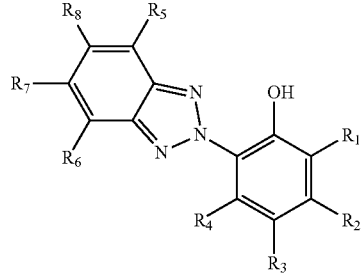

Formula I wherein if $R^1$ is an —O—$R^9$, a —N—$R^9R^{10}$, a —B(O$R^{18}$)(O$R^{19}$) group, or a —Si$R^{20}{}_3$ group wherein $R^9$ is selected from an alkyl group, or an aryl group, and $R^{10}$ is selected from a hydrogen atom, an alkyl group, an alkenyl group, an aryl group, or a heteroatom-containing group comprising one or more oxygen, nitrogen, sulfur, or phosphorous atoms, or $R^9$ and $R^{10}$ together with the atoms connecting form a heterocyclic ring structure, each $R^{18}$ and $R^{19}$ is independently a hydrogen atom, an alkyl group, an aryl group, or $R^{18}$ and $R^{19}$ together with the atoms connecting form a heterocyclic ring structure, each $R^{20}$ group is an alkyl group; and each $R^2$, $R^3$, $R^4$, $R^5$, $R^6$, $R^7$, and $R^8$, independently is a hydrogen atom, an alkyl group, an alkenyl group, an aryl group, or a halogen atom; and $R^3$ is an alkyl group with 8 carbon atoms.

2. The composition of claim 1, wherein $R^1$ comprises an —O—$R^9$ group wherein $R^9$
an alkyl group with 1-20 carbon atoms; or
an aryl group.

3. The composition of claim 2, wherein $R^9$ is:
an alkyl group with 1-6 carbon atoms; or
an aryl group comprising a substituted phenyl group.

4. The composition of claim 1, wherein $R^1$ comprises a —N—$R^9R^{10}$ group:
wherein $R^9$ is selected from an alkyl group with 1-20 carbon atoms; or
an aryl group;
$R^{10}$ is selected from a hydrogen atom or an alkyl group with 1-6 carbon atoms.

5. The composition of claim 4, wherein $R^9$ is selected from:
an alkyl group with 1-6 carbon atoms; or
an aryl group comprising a 3-alkyl substituted phenyl group, wherein the alkyl substituted group has 1-6 carbon atoms;
$R^{10}$ is a hydrogen atom.

6. The composition of claim 1, wherein $R^1$ comprises a hydrogen atom; $R^3$ is an alkoxy group comprising 4 carbon atoms; and each $R^2$, $R^4$, $R^5$, $R^6$, $R^7$, and $R^8$, independently is a hydrogen atom.

7. The composition of claim 2, wherein $R^1$ comprises an —O—$R^9$ group wherein $R^9$ is an alkyl group with 4 carbon atoms.

8. The composition of claim 2, wherein $R^1$ comprises an —O—$R^9$ group wherein $R^9$ comprises an aryl group comprising a 3-methyl phenyl group, or a 4-methyl phenyl group.

9. The composition of claim 4, wherein $R^1$ comprises an —N—$R^9R^{10}$ group wherein $R^9$ is an alkyl group with 1 carbon atom, or an alkyl group with 6 carbon atoms;
$R^{10}$ is a hydrogen atom.

10. The composition of claim 4, wherein $R^1$ comprises an —N—$R^9R^{10}$ group wherein $R^9$ is an aryl group comprising an alkyl substituted phenyl group, wherein the alkyl substituted group has 1-20 carbon atoms;
$R^{10}$ is a hydrogen atom.

11. The composition of claim 10, wherein the alkyl substituted phenyl group is a 4-hexyl phenyl group.

12. The composition of claim 1, comprising the structure of Formula II:

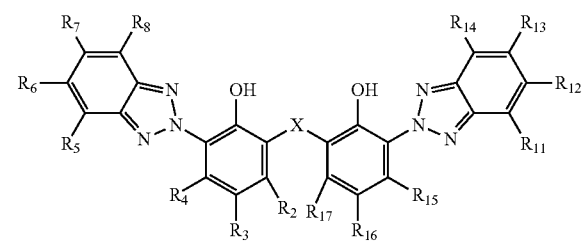

Formula II wherein X comprises an —O—, —$NR^{10}$—, —S(O)—, —S(O)$_2$—, or —S— linking group where $R^{10}$ is selected from a hydrogen atom, an alkyl group, or an aryl group, each $R^2$, $R^3$, $R^4$, $R^5$, $R^6$, $R^7$, $R^8$, $R^{11}$, $R^{12}$, $R^{13}$, $R^{14}$, $R^{15}$, $R^{16}$, and $R^{17}$, independently independently is a hydrogen atom, an alkyl group, an alkenyl group, an aryl group, or a halogen atom; and $R^3$ and $R^{16}$ are each an alkyl group with 8 carbon atoms.

13. The composition of claim 12, wherein X is an —$NR^{10}$— linking group where $R^{10}$ is selected from a hydrogen atom, an alkyl group comprising 1-3 carbon atoms.

$R^3$ and $R^{16}$, each comprises an alkyl group with 1-20 carbon.

14. The composition of claim 12, wherein X comprises an —O— linking group.

15. The composition of claim 12, wherein X comprises an —$NR^{10}$— linking group where $R^{10}$ is a hydrogen atom; and each $R^2$, $R^4$, $R^5$, $R^6$, $R^7$, $R^8$, $R^{11}$, $R^{12}$, $R^{13}$, $R^{14}$, $R^{15}$, and $R^{17}$, independently is selected from a hydrogen atom, an alkyl group, an alkenyl group, an aryl group, or a halogen atom.

16. The composition of claim 12, wherein X comprises an —$NR^{10}$— linking group where $R^{10}$ is a methyl group; and each $R^2$, $R^4$, $R^5$, $R^6$, $R^7$, $R^8$, $R^{11}$, $R^{12}$, $R^{13}$, $R^{14}$, $R^{15}$, and $R^{17}$, independently is selected from a hydrogen atom, an alkyl group, an alkenyl group, an aryl group, or a halogen atom.

17. The composition of claim 12, wherein X comprises an —O— linking group; and each $R^2$, $R^4$, $R^5$, $R^6$, $R^7$, $R^8$, $R^{11}$, $R^{12}$, $R^{13}$, $R^{14}$, $R^{15}$, and $R^{17}$, independently is selected from a hydrogen atom, an alkyl group, an alkenyl group, an aryl group, or a halogen atom.

* * * * *

UNITED STATES PATENT AND TRADEMARK OFFICE
CERTIFICATE OF CORRECTION

| | |
|---|---|
| PATENT NO. | : 10,919,867 B2 |
| APPLICATION NO. | : 15/741647 |
| DATED | : February 16, 2021 |
| INVENTOR(S) | : Kelly Anne Volp et al. |

It is certified that error appears in the above-identified patent and that said Letters Patent is hereby corrected as shown below:

In the Claims

Column 49
Line 5, In Claim 1, after "group;", delete "and".
Line 6, In Claim 1, after "$R^2$,", delete "$R^3$,".
Line 10, In Claim 2, delete "comprises" and insert -- is --, therefor.
Line 11, In Claim 2, after "wherein $R^9$", insert -- is selected from: --.
Line 17, In Claim 4, delete "comprises" and insert -- is --, therefor.
Line 31, In Claim 6, delete "comprises" and insert -- is --, therefor.
Line 35, In Claim 7, delete "comprises" and insert -- is --, therefor.
Line 38, In Claim 8, delete "comprises" and insert -- is selected from --, therefor.
Line 42, In Claim 9, delete "comprises" and insert -- is --, therefor.
Line 46, In Claim 10, delete "comprises" and insert -- is --, therefor.

Column 50
Line 19 (Approx.), In Claim 12, delete "comprises" and insert -- is selected from --, therefor.
Line 23, In Claim 12, after "$R^2$,", delete "$R^3$,".
Line 24, In Claim 12, before "and $R^{17}$", delete "$R^{16}$,".
Line 24, In Claim 12, delete "independently independently" and insert -- independently --, therefor.
Line 29, In Claim 13, insert -- or -- between "hydrogen atom," and "an alkyl group".
Line 31-32, In Claim 13, after "atoms", delete "$R^3$ and $R^{16}$, each comprises an alkyl group with 1-20 carbon".
Line 33, In Claim 14, delete "comprises" and insert -- is --, therefor.
Line 35, In Claim 15, delete "comprises" and insert -- is --, therefor.
Line 40, In Claim 16, delete "comprises" and insert -- is --, therefor.
Line 45, In Claim 17, delete "comprises" and insert -- is --, therefor.

Signed and Sealed this
Twenty-first Day of November, 2023

Katherine Kelly Vidal
*Director of the United States Patent and Trademark Office*